United States Patent
Newman

(10) Patent No.: US 10,743,744 B2
(45) Date of Patent: Aug. 18, 2020

(54) ENDOSCOPE WITH MULTIDIRECTIONAL EXTENDIBLE ARMS AND TOOL WITH INTEGRATED IMAGE CAPTURE FOR USE THEREWITH

(71) Applicant: Endopodium, Inc., Escondido, CA (US)

(72) Inventor: Allen Newman, Rancho Santa Fe, CA (US)

(73) Assignee: ENDOPODIUM, INC., Escondido, CA (US)

( * ) Notice: Subject to any disclaimer, the term of this patent is extended or adjusted under 35 U.S.C. 154(b) by 247 days.

(21) Appl. No.: 15/487,381

(22) Filed: Apr. 13, 2017

(65) Prior Publication Data

US 2017/0296036 A1     Oct. 19, 2017

Related U.S. Application Data

(60) Provisional application No. 62/322,121, filed on Apr. 13, 2016.

(51) Int. Cl.
*A61B 1/00* (2006.01)
*A61B 1/313* (2006.01)
(Continued)

(52) U.S. Cl.
CPC ........ *A61B 1/00087* (2013.01); *A61B 1/0008* (2013.01); *A61B 1/00154* (2013.01); *A61B 1/3132* (2013.01); *A61B 17/3421* (2013.01); *A61B 1/00016* (2013.01); *A61B 1/00096* (2013.01); *A61B 1/00181* (2013.01); *A61B 1/00183* (2013.01); *A61B 1/05* (2013.01); *A61B 1/051* (2013.01); *A61B 17/3201* (2013.01);
(Continued)

(58) Field of Classification Search
CPC .............. A61B 1/0008; A61B 1/00087; A61B 1/00181; A61B 1/00183; A61B 2017/3484; A61B 2017/3492; A61B 1/0052
USPC ........................... 604/108; 600/137; 606/198
See application file for complete search history.

(56) References Cited

U.S. PATENT DOCUMENTS 5,197,971 A * 3/1993 Bonutti .............. A61B 17/0218
604/105
5,279,575 A   1/1994 Sugarbaker
(Continued)

*Primary Examiner* — Aaron B Fairchild
(74) *Attorney, Agent, or Firm* — Scott H. Davison; Musick Davison LLP

(57) ABSTRACT

An endoscope and methods of use thereof is provided with at least one multi-functional, multi-directional arm supporting a plurality of imaging, lighting and other sensory elements. The multi-functional arms provide a mounting platform upon which cameras, lights and sensors may be mounted to generate multiple-angled images and video, arena-like lighting and other data relevant to performing a diagnostic or MIS procedure. The multi-directional arms may be inserted through a single portal in the endoscope and deployed in multiple directions from a single portal once inserted into a body cavity. The pitch, roll, length and curvature of each of the extending arms may be individually or jointly adjusted to create a customized view of an internal space during an endoscopic procedure. The extending arms may also include communication elements to wirelessly transmit the images and other data generated by the sensory elements to a remote computing and display device.

7 Claims, 24 Drawing Sheets

(51) Int. Cl.
  *A61B 17/34* (2006.01)
  *A61B 1/05* (2006.01)
  *A61B 17/3201* (2006.01)
  *A61B 17/00* (2006.01)
  *A61B 90/00* (2016.01)

(52) U.S. Cl.
  CPC ....... *A61B 90/361* (2016.02); *A61B 2017/003* (2013.01); *A61B 2017/3484* (2013.01); *A61B 2017/3492* (2013.01)

(56) References Cited

U.S. PATENT DOCUMENTS

| | | | |
|---|---|---|---|
| 5,857,999 | A | 1/1999 | Quick et al. |
| 6,066,090 | A | 5/2000 | Yoon |
| 2005/0085691 | A1* | 4/2005 | Nakao ................ A61B 1/00071 600/128 |
| 2009/0030276 | A1 | 1/2009 | Saadat et al. |
| 2011/0306832 | A1 | 12/2011 | Bassan et al. |
| 2014/0094655 | A1* | 4/2014 | Newman .............. A61B 1/0008 600/109 |

* cited by examiner

ENDOSCOPE WITH MULTIDIRECTIONAL EXTENDIBLE ARMS AND TOOL WITH INTEGRATED IMAGE CAPTURE FOR USE THEREWITH

BACKGROUND

Field of the Invention

The embodiments described herein are related to an endoscope with a plurality of multifunctional extending arms and an endoscopic tool with an integrated camera for use therewith, and more particularly to an endoscope with a plurality of multi-functional and multi-directional extending arms upon which a plurality of cameras, lighting and other sensory elements may be mounted and moved into various positions, all of which can be used in conjunction with the camera-mounted endoscopic tool.

Related Art

An endoscope is a medical optics device which is used to look inside the human body. It may include a tube known as a cannula which contains optical elements and a light source for capturing images on a distal end of the tube which are viewed by a user outside the body through a monitor or an eyepiece. The endoscope is commonly used for diagnostics and for performing minimally-invasive surgery (MIS), where only small openings are made in the dermis and body walls through which the endoscope is inserted. A user, such as a surgeon performing a medical procedure, will insert the endoscope through an opening in the body, after which the surgeon may insert a medical instrument through another opening with which they can perform the medical procedure while viewing it through the optics in the endoscope.

Endoscopes are limited by the optics implemented in the endoscope and the resulting ability to clearly view an area within the human body while performing a medical procedure. When the optical elements of the endoscope are inserted separately from the medical instrument, it is difficult to view the medical instrument and the work that is being done. Additionally, manipulating the medical instrument to perform the medical procedure and the endoscope to ensure proper viewing of the procedure is often exceedingly difficult, requiring careful manipulation and coordination to move both devices. In some situations, more than one medical instrument is inserted and must be manipulated simultaneously with the other inserted medical instruments all while continuously repositioning the endoscope for a proper view. Additionally, in cases where the medical instrument must move around an object within the body, such as an organ, tissue, bone, etc., the endoscope may be unable to follow the medical instrument and provide adequate images of an area of interest. The benefits of performing MIS are hampered by the lack of visual and other information available to the surgeon.

SUMMARY

Embodiments described herein provide an endoscope and methods of use thereof which includes at least one multi-functional and multi-directional extending arm supporting a plurality of imaging, lighting and other sensory elements. The multi-functional extending arms provide a mounting platform upon which cameras, lights and sensors may be mounted to generate multiple-angled images and video, arena-like lighting and other data relevant to performing a medical diagnostic or minimally-invasive surgical (MIS) procedure. The multi-functional extending arms may be inserted through a single portal in the endoscope and extended outward in multiple directions from the single portal once inserted into a body cavity. The endoscope may also include support arms which support the extending arms within the body cavity and a stabilization plate which anchors the endoscope to an external surface of the body. The extending arms may also include communication elements to transmit, either wired or wirelessly, the images and other data generated by the sensory elements to a remote computing and display device.

Embodiments described herein also provide a medical instrument with an integrated image capture device for use with an endoscope in minimally-invasive surgery (MIS). The image capture device may be mounted near an end portion of the medical instrument where the medical instrument interfaces with tissue so that images can be generated anywhere the medical instrument is directed without requiring manipulation and guidance of a separate endoscope. In one embodiment, the image capture device may be a CMOS camera that can easily be implemented on a medical instrument used for MIS. One or more lighting devices may also be implemented into an end portion of the medical instrument to provide sufficient illumination for the image capture device. In one embodiment, the medical instrument may be inserted into a body cavity through a cannula in the endoscope.

In one aspect of the invention, an endoscope with a multifunctional extending arm comprises a central shaft with a distal end and a proximal end, wherein the distal end is configured to be inserted through a cannula and into a body cavity; and a plurality of multi-functional arms positioned at the distal end of the central shaft, wherein the multi-functional arms are configured to deploy outward from the central shaft through actuation of a rotatable dial at the proximal end of the central shaft.

In another aspect of the invention, the endoscope further comprising a cannula disposed around the endoscope and bisecting a body cavity wall, the cannula comprising: a stabilization plate positioned around a circumference of the cannula and disposed against an exterior surface of the body cavity wall; and a plurality of deployable support tabs extending from a distal surface of the cannula and disposed against an interior surface of the body cavity wall; wherein the stabilization plate is in mechanical communication with the plurality of support tabs such that movement of the stabilization plate along a longitudinal axis of the cannula results in deployment or retraction of the support tabs.

In a further aspect of the invention, a method of performing an endoscopic procedure comprises the steps of: inserting a central shaft into a body cavity through an opening in a body cavity wall provided by a cannula, the central shaft including a distal end and a proximal end; deploying a plurality of multi-functional arms positioned at the distal end of the central shaft outward from the central shaft and into the body cavity through actuation of a rotatable dial at the proximal end of the central shaft.

In a yet further aspect of the invention, the method of performing the endoscopic procedure further comprises disposing a cannula into the body cavity wall prior to inserting the endoscope, wherein disposing the cannula further comprises: disposing a stabilization plate positioned around a circumference of the cannula against an exterior surface of the body cavity wall; and deploying a plurality of support tabs extending from a distal surface of the cannula against an interior surface of the body cavity wall; wherein the stabilization plate is in mechanical communication with the plurality of support tabs such that movement of the stabilization plate along a longitudinal axis of the cannula results in deployment or retraction of the support tabs.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which.

DETAILED DESCRIPTION

Embodiments described herein provide an endoscope and methods of use thereof which includes at least one multi-functional and multi-directional extending arm supporting a plurality of imaging, lighting and other sensory elements. The multi-functional extending arms provide a mounting platform upon which cameras, lights and sensors may be mounted to generate multiple-angled images and video, arena-like lighting and other data relevant to performing a medical diagnostic or minimally-invasive surgical (MIS) procedure. A cannula with a set of internal support arms and external stabilization plate tabs is provided for securing an opening formed by a trocar, after which the multi-directional extending arms may be inserted through the opening and into the body cavity, then deployed outward in multiple directions from the opening. The pitch, roll, length and curvature of each of the extending arms may be individually or jointly adjusted to create a customized view of an internal space during an endoscopic procedure. The endoscope or extending arms may also include communication elements to transmit, either wired or wirelessly, the images and other data generated by the sensory elements to a remote computing and display device.

Embodiments described herein also provide a medical instrument in the form of an endoscopic tool with at least one integrated image capture device positioned at an interfacing end of the medical instrument, where the medical instrument interfaces with tissue during a minimally-invasive surgical (MIS) procedure. The medical instrument may be any type of endoscopic tool used during MIS, such as scissors, graspers, dissectors, staplers, etc. The interfacing end of the medical instrument may then be the portion of the medical instrument where the actual scissor blades, grasper clamps, staple arms, etc. are located. In one embodiment, one or more image capture devices may be integrated proximate to an interfacing end and extend from one or more side portions so that a user can view the movement of the medical instrument as it performs its function from multiple angles, including via a three-dimensional image generated from cameras extending from opposing side portions.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

Endoscope Assembly

Figure 1:
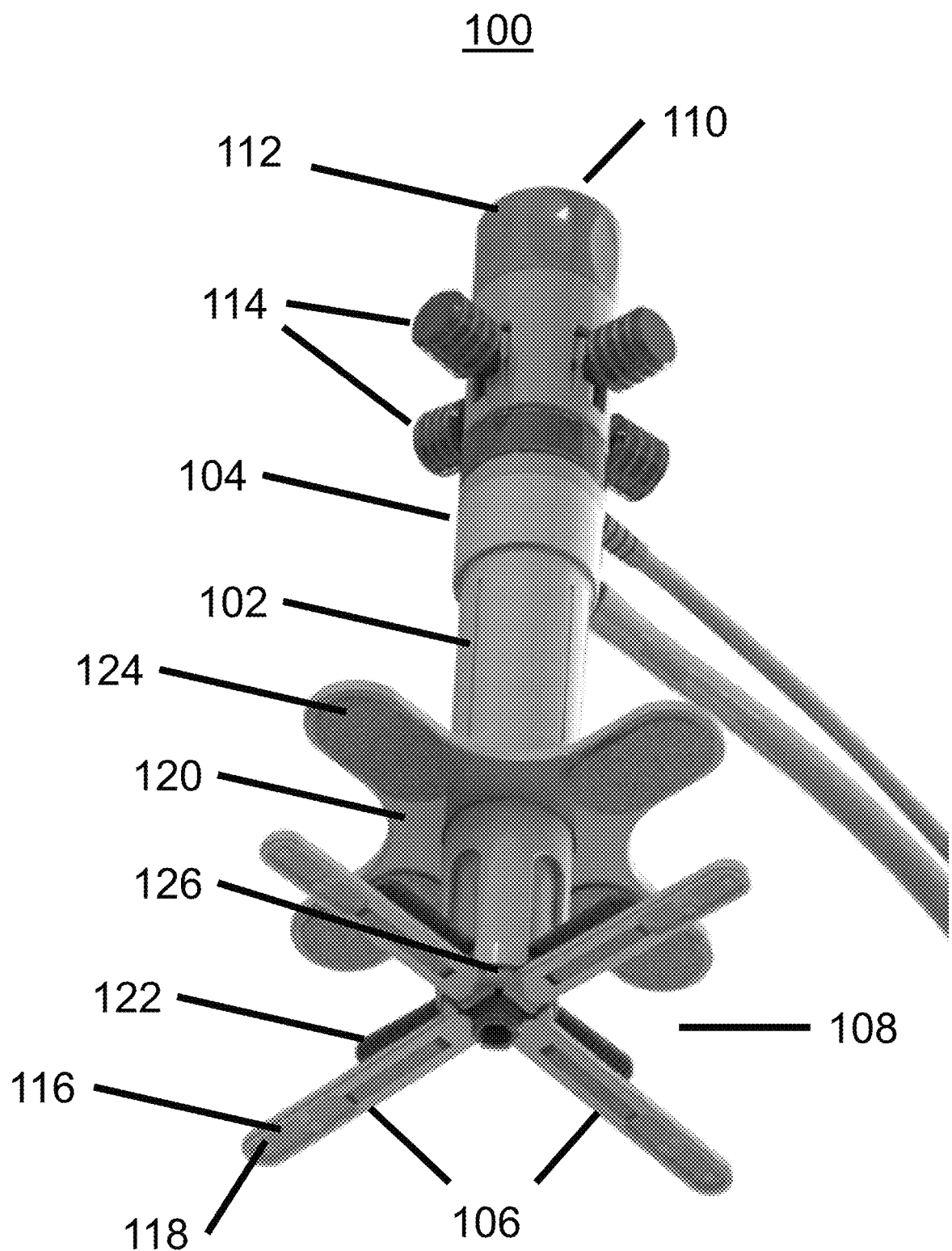
FIG. 1 is an illustration of an endoscope with multi-functional and multi-directional extending arms supporting a plurality of imaging, lighting and other sensory elements according to an embodiment of the invention.

In one embodiment, the endoscope includes a plurality of independently-adjustable arms which deploy outward from a central endoscopic opening. A complete endoscope assembly 100 in a fully-deployed configuration is illustrated in FIG. 1, which includes a cannula 102 serving as the conduit between a body cavity and the external environment through which the camera platform 104 comprising a central shaft with a plurality of multi-functional multi-directional arms 106 may be inserted. The arms 106 are positioned at a distal end 108 of the camera platform 104 and primarily disposed within the body cavity, while a proximal end 110 of the camera platform 104 is primarily disposed outside of the body cavity and contains control mechanisms for controlling the arms 106, including an arm deployment dial 112 and arm control joysticks 114 (the functions of which will be described further herein). In the fully-deployed configuration illustrated herein, each of the arms 106 extends outwardly from the center shaft of the cannula 102 at approximately ninety (90) degree angles with respect to each adjacent arm. With each arm configured with image capture devices 116, lighting elements 118 and other sensors, the endoscope is able to provide a wide-angle view of an internal body cavity from multiple angles; additionally providing the ability to create three-dimensional (3D) images in real-time for viewing by a medical professional performing an endoscopic procedure.

The cannula 102 is primarily a hollow cylindrical portion which receives the distal end 108 of the camera platform 104 for passing into the body cavity, but which also includes two stabilizing devices for maintaining the cannula and endoscope in position on the body cavity wall. The first is a stabilization plate 120 which is disposed around the cannula and which is configured to be positioned against an exterior surface of the abdomen or other body cavity. Within the body cavity, the cannula includes a plurality of support arms 122 which are initially disposed within the cannula wall but which can be deployed outwardly within the body cavity to rest against an interior surface of the abdominal wall. The support arms 122 are in mechanical communication with the stabilization plate such that actuation of the stabilization plate in a downward motion along the longitudinal axis of the cannula 102 causes the deployment of the support arms 122, as will be described further below. The support arms 122 may also be configured to deploy in a similar configuration to the multi-functional arms 106 in order to prevent the multi-functional arms 106 from impacting against the body cavity wall. In one embodiment, the stabilization plate 120 is shaped with a plurality of tabs 124 which extend away from the cannula and which correspond to the position of the multi-functional arms 106 within the body cavity in order to provide an external guide to a user with regard to the location of the multi-functional arms 106 within the body cavity. A separate set of alignment tabs 126 extend from the cannula 102 to a position between each of the multi-functional arms 106 at the distal end 108 of the camera platform 102 in order to translate rotation of the cannula 102 along its longitudinal axis into corresponding rotation of the multifunctional arms 106 in order to maintain alignment of the multifunctional arms 106 and the tabs 124 of the stabilization plate 120.

Figure 2:
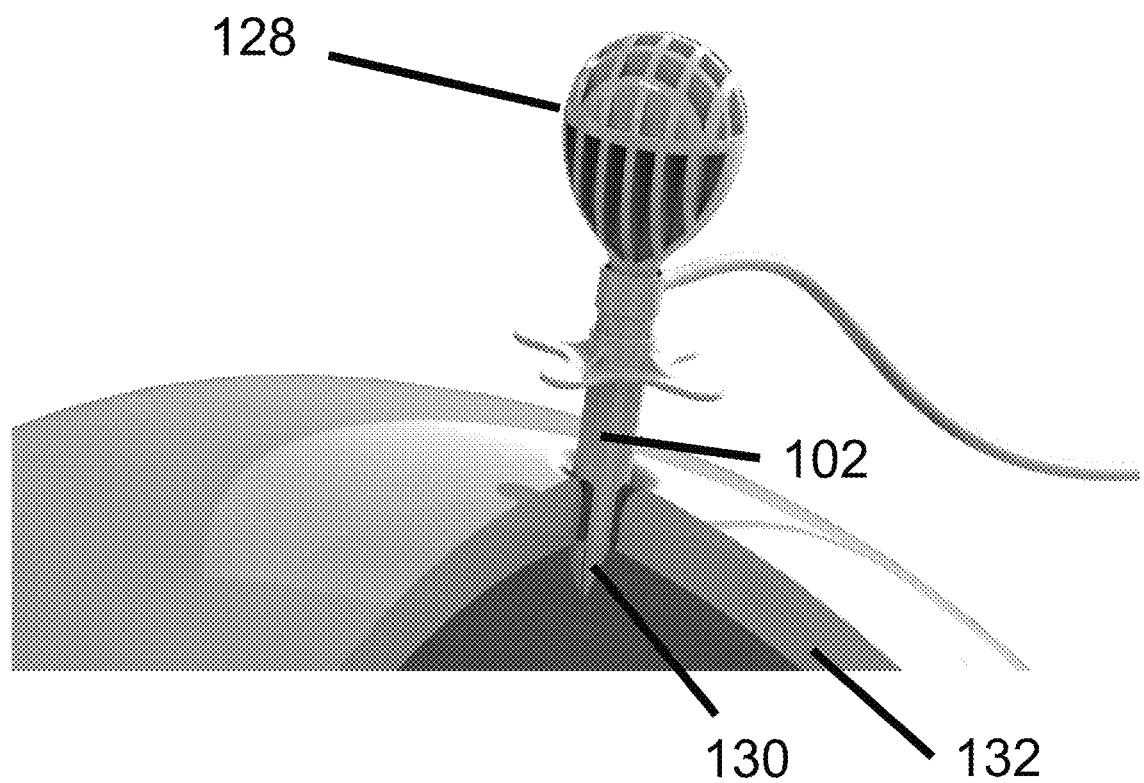
FIG. 2 is an illustration of a trocar and cannula being inserted into an abdominal cavity, according to an embodiment of the invention.

FIG. 2 is an illustration of a process of inserting a trocar 128 with a sharp distal point 130 through the cannula 102 to create an opening in an abdominal wall 132 of a human or animal. The trocar 128 creates the opening, after which it is removed and replaced with the camera platform 104.

Figure 3A:
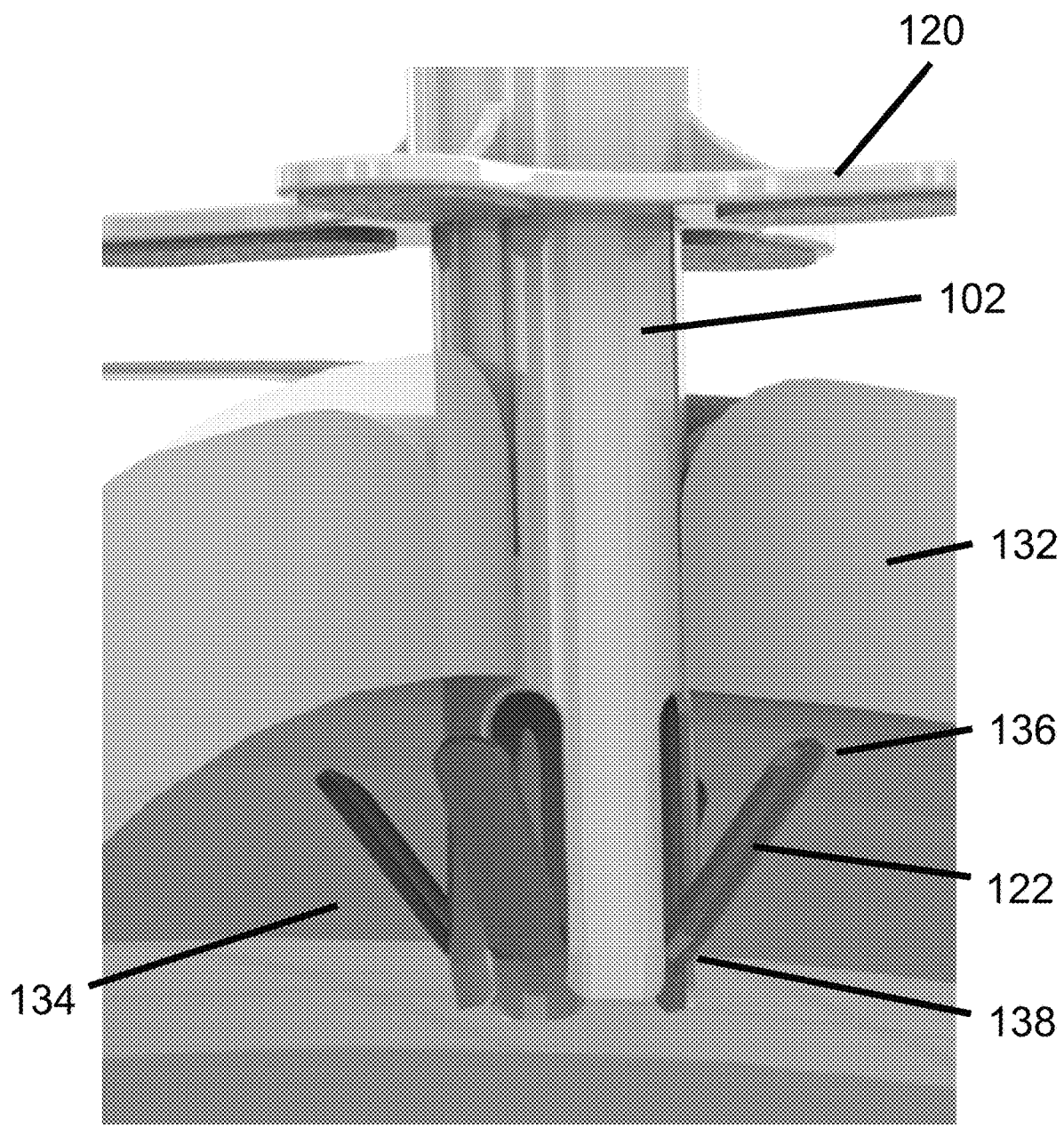
FIG. 3A illustrates an initial configuration of the cannula during a process of extending interior support arms disposed on the cannula and positioning an exterior stabilization plate disposed around the cannula to secure the cannula onto interior and exterior sides of an abdominal wall, according to one embodiment of the invention.
Figure 3B:
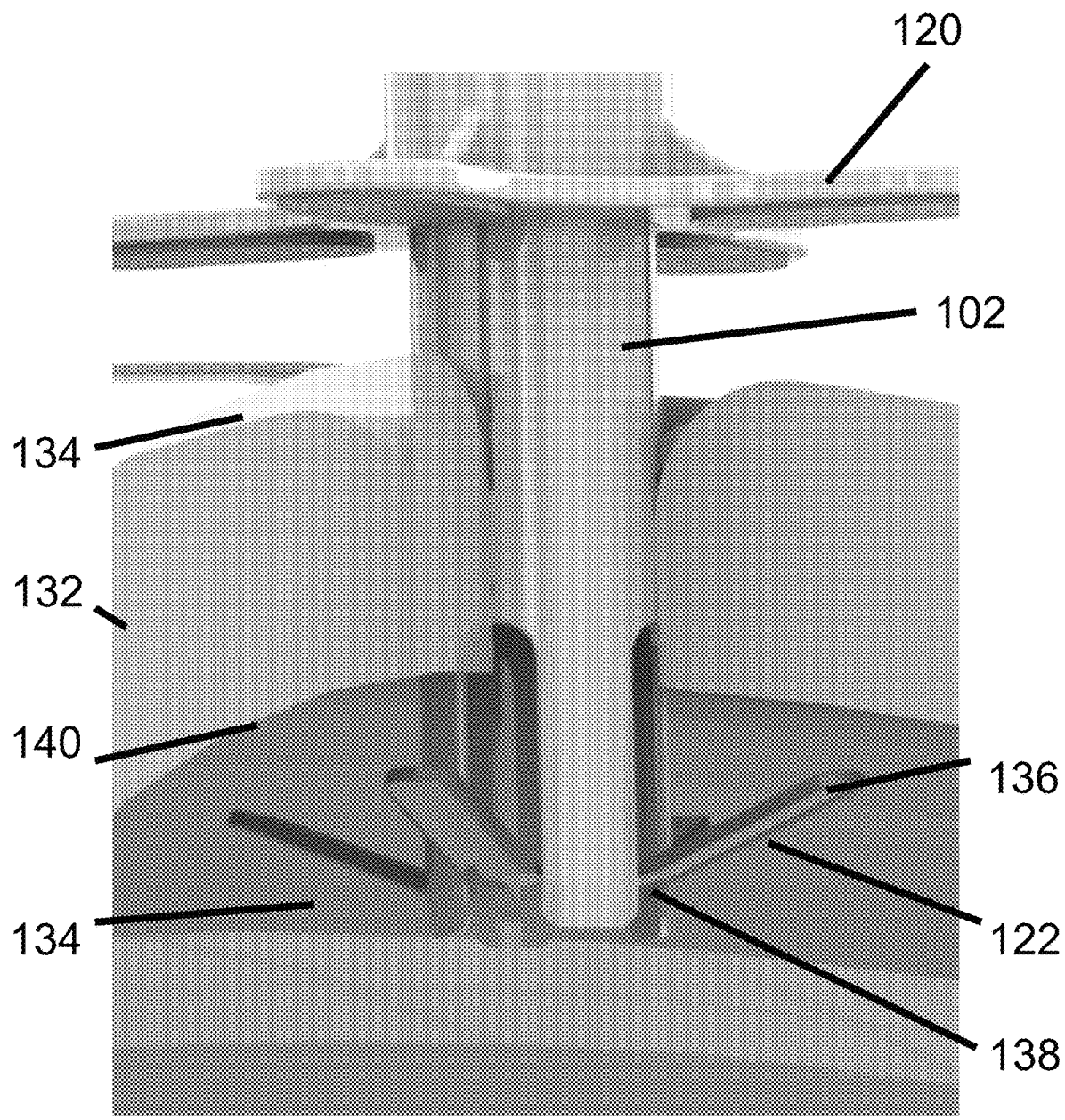
FIG. 3B illustrates an intermediate configuration of the interior support arms during the process of extending the interior support arms, according to one embodiment of the invention.
Figure 3C:
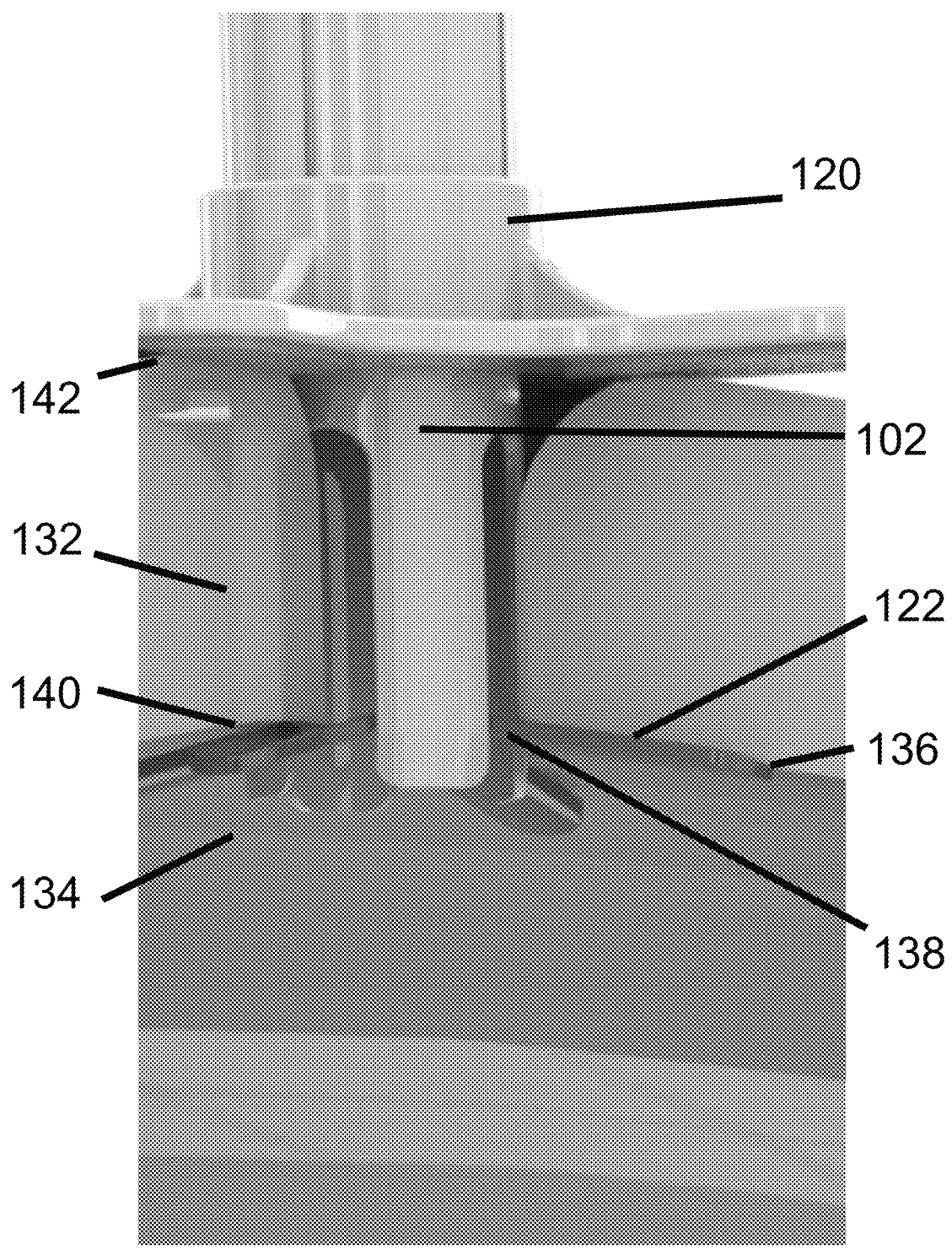
FIG. 3C illustrates a secured configuration of the interior support arms and a final secure position of the exterior stabilization plate, during one embodiment of the invention.

FIGS. 3A-3C illustrate a process of securing the cannula 102 to the abdominal or body cavity wall 132 using the stabilizing devices previously described. In FIG. 3A, the plurality of support arms 122 which were previously disposed flush against an outer wall of a distal end 134 of the cannula 102 are deployed through actuation of the stabilization plate in a downward motion toward the body cavity wall 132 such that a distal end 136 of each support arm 122 begins to extend away from the cannula 102, while a proximal end 138 is rotatably anchored to the distal end 134 of the cannula. As mentioned above, the stabilization plate is configured to be in mechanical communication with the support arms 122 such that movement of the stabilization plate in an upward or downward motion acts to retract or deploy, respectively, the support arms 122. The stabilization plate 120 remains in an unsecured configuration separated from the body cavity wall 132.

In FIG. 3B, the support arms 122 have further extended away from the cannula 102, while the cannula itself has begun to be withdrawn out of the body cavity to bring the support arms 122 closer to an interior surface 140 of the body cavity wall. In FIG. 3C, the support arms 122 have fully deployed into their fully extended position at an angle approximately perpendicular to the cannula 102, and the cannula 102 has been retracted from the body cavity such that it is substantially retained within the body cavity wall 132, while also bringing the support arms 122 flush with the interior surface 140 of the body cavity wall. It is important to note that as the interior surface 140 of the body cavity wall 132 is not necessarily disposed on a planar surface, the support arms 122 may also be able to individually deploy at varying angles with respect to the cannula that allow it to provide adequate contact with the interior surface of the abdominal wall. On the surface of the cannula 102 on the outside of the body, the stabilization plate 120 has now been lowered into a flush position against an exterior surface 142 of the body cavity wall, where it works in conjunction with the support arms 122 to maintain the position of the cannula on the body cavity wall 132, something which is beneficial during an endoscopic procedure that may require the continued insertion and removal of the camera platform 104 and other tools through the opening in the cannula 102. FIG. 3C also more clearly illustrates the overall disposition of the stabilization plate 120 around the circumference of the cannula 102 which allows the stabilization plate to actuate down and up to deploy and retract the support arms 122.

Figure 4A:
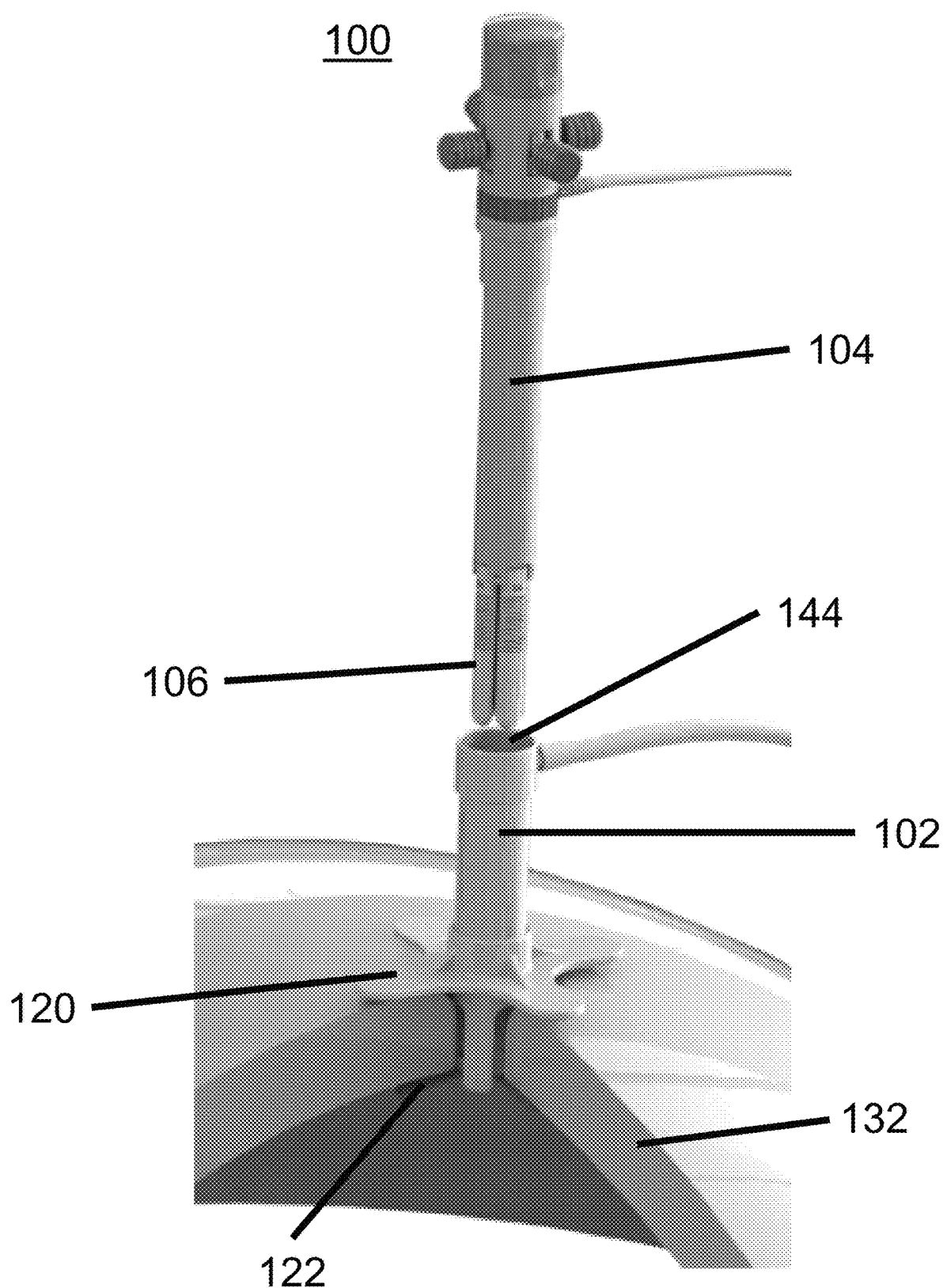
FIG. 4A illustrates a side view of a process of inserting a camera platform into the abdominal cavity after the trocar is removed, according to one embodiment of the invention.
Figure 4B:
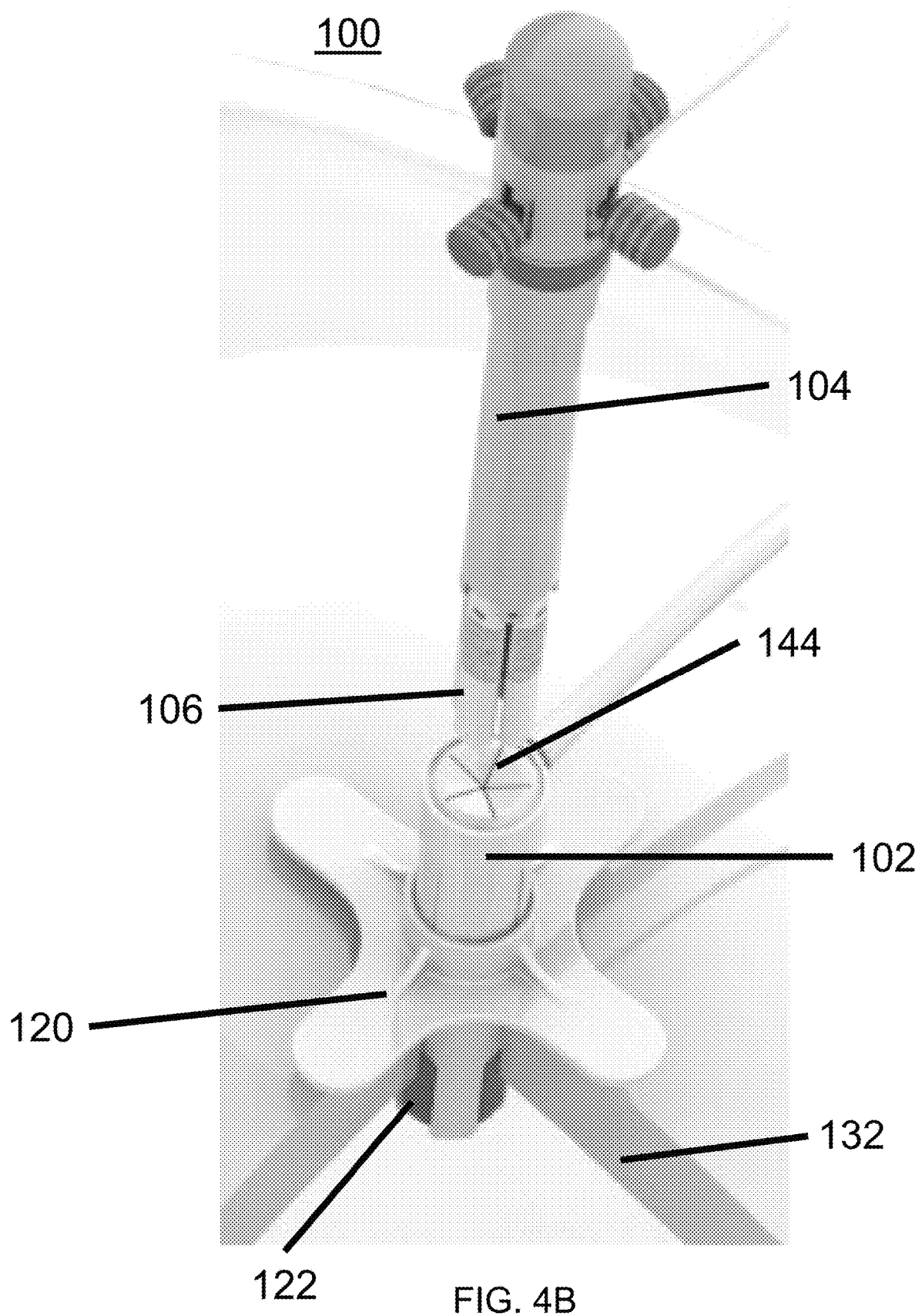
FIG. 4B is a further top-down perspective view illustration of the camera platform being inserted into the abdominal cavity, according to one embodiment of the invention.

FIG. 4A illustrates a side perspective view of the cannula 102—now secured to the body cavity wall 132 via the stabilization plate 120 and support arms 122 and with the trocar fully removed—in preparation for receiving the camera platform 104 through the opening 144. The multifunctional arms 106 are in an initial undeployed configuration parallel to the longitudinal axis of the camera platform 104 so that they can fit into the opening 144. FIG. 4B is a top perspective view illustration of the camera platform 104 prior to insertion through the opening 144 of the cannula.

Figures 5A, 5B, 5C:
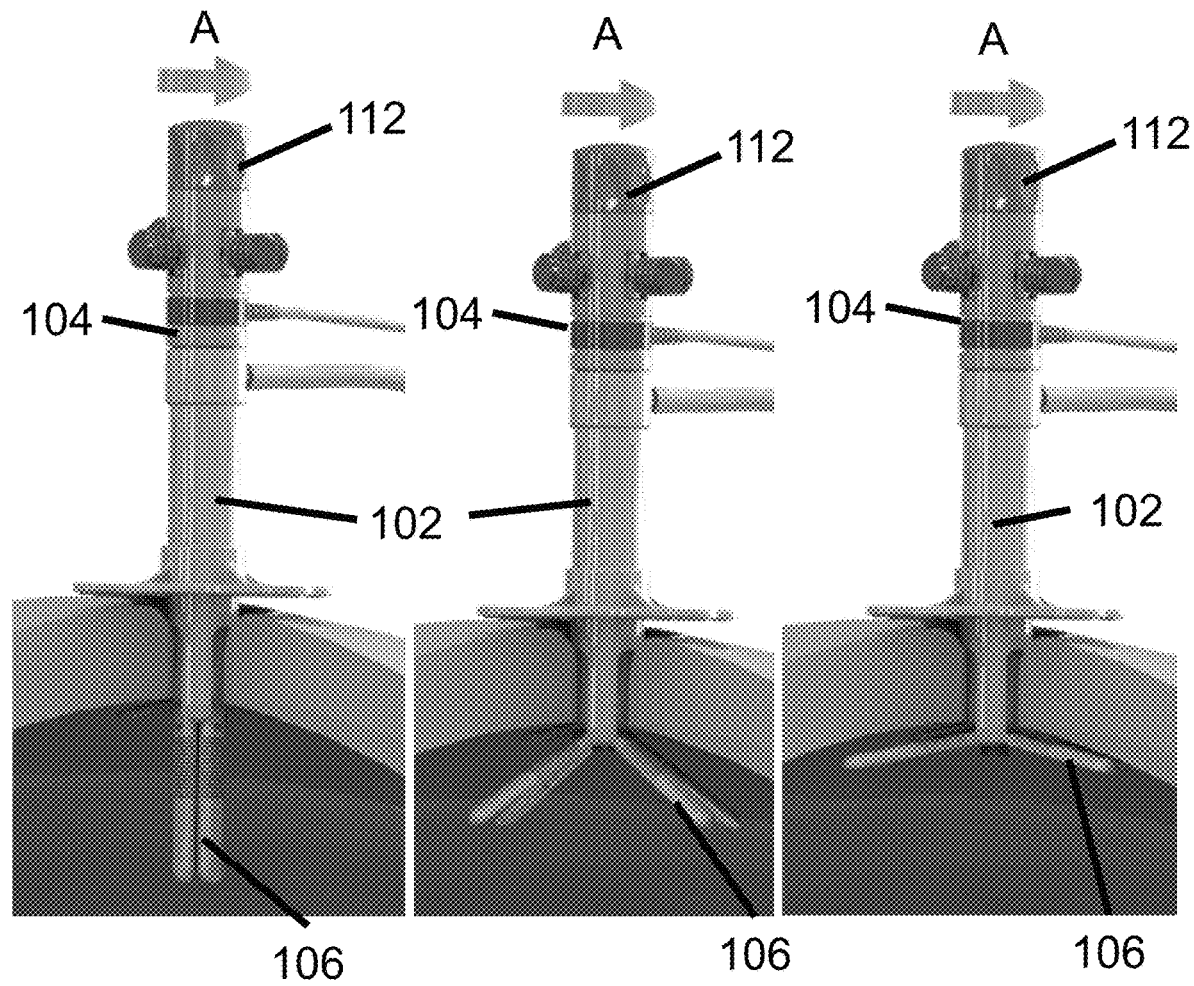
FIG. 5A illustrates an initial configuration of extendible arms at the beginning of a process of deploying the extendible arms from the endoscope, according to one embodiment of the invention.
FIG. 5B illustrates an intermediate configuration of the extendible arms during the process of deploying the extendible arms from the endoscope, according to one embodiment of the invention.
FIG. 5C illustrates a fully-deployed configuration of the extendible arms within the abdominal cavity, according to one embodiment of the invention.

FIGS. 5A-5C illustrates a process of deploying the extendible arms, which may be done by rotating the arm deployment dial 112 at the proximal end of the camera platform 104, as shown by the circular arrow A. This rotational deployment provides a first level of control of the angle and extension of the arms 106, as the arms may be configured to stop the deployment at any position between an initial, undeployed configuration (as shown in FIG. 5A) and a final, fully deployed configuration (as shown in FIG. 5C).

FIG. 5A illustrates the undeployed configuration of the multifunctional arms 106 where the arms are parallel to the longitudinal axis of the camera platform itself 104. In FIG. 5B, after partial rotation of the arm deployment dial 112, the multifunctional arms 106 have begun to deploy away from the camera platform 104, primarily by changing the pitch of each multifunctional arm 106 with respect to a lateral axis of the camera platform 104 and ultimately with respect to the lateral axis of each multifunctional arm 106. In FIG. 5C, a fully-deployed configuration of the multifunctional arms 106 is illustrated, and is the result of the complete actuation of the arm deployment dial 112. The fully-deployed configuration of the multifunctional arms generally refers to a position of the multifunctional arms 106 where the lateral axis is approximately perpendicular to the lateral axis of the camera platform 104. When the multifunctional arms have been at least partially deployed, they can be used to capture images of the interior of the body cavity from different angles to provide a user with a more accurate picture of the area where the procedure is being accomplished.

Figure 6A:
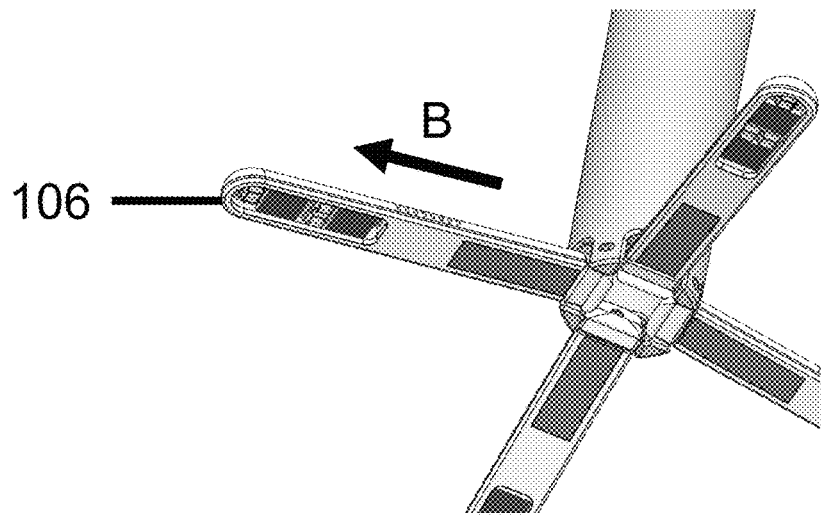
FIG. 6A illustrates an initial configuration of the extendible arms prior to a process of extending the length of the extendible arms outward, according to one embodiment of the invention.
Figure 6B:
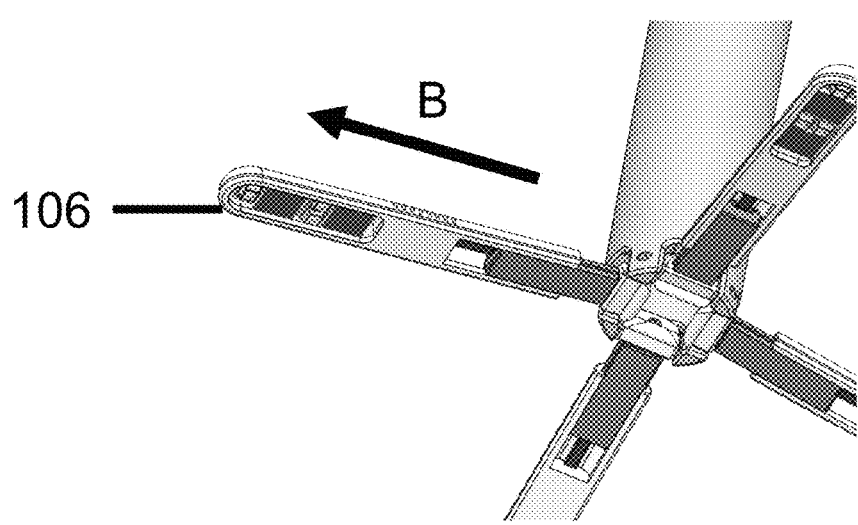
FIG. 6B illustrates an intermediate configuration of the extendible arms during the process of extending the length of the extendible arms outward, according to one embodiment of the invention.
Figure 6C:
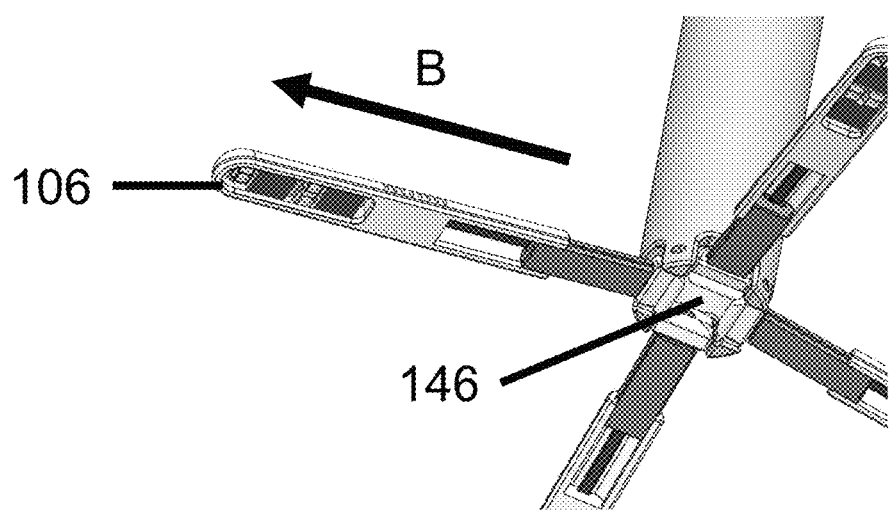
FIG. 6C illustrates a final extended configuration of the extendible arms in a full-length outward extension, according to one embodiment of the invention.

FIGS. 6A-6C illustrate a process of extending a length of the multifunctional, arms 106 outward from a central opening of the camera platform 104 in order to provide wider and additional angles for each arm. FIG. 6A illustrates an initial, un-extended configuration of the multifunctional arms 106 prior to any extension. FIG. 6B illustrates an intermediate configuration of the multifunctional arms when the arms 106 have begun to extend longitudinally along their longitudinal axes shown by arrow B, and FIG. 6C illustrates a final, fully-extended configuration of the multifunctional arms 106 at a maximum distance from the central opening 146 of the camera platform 104. The additional extensions of the arms may be provided by a single control to extend all arms simultaneously or by individual control in order to extend each arm individually, and as such may be accomplished by, for example, further rotation of the arm deployment dial 112 or by actuation of the individual joysticks 114.

Figure 7A:
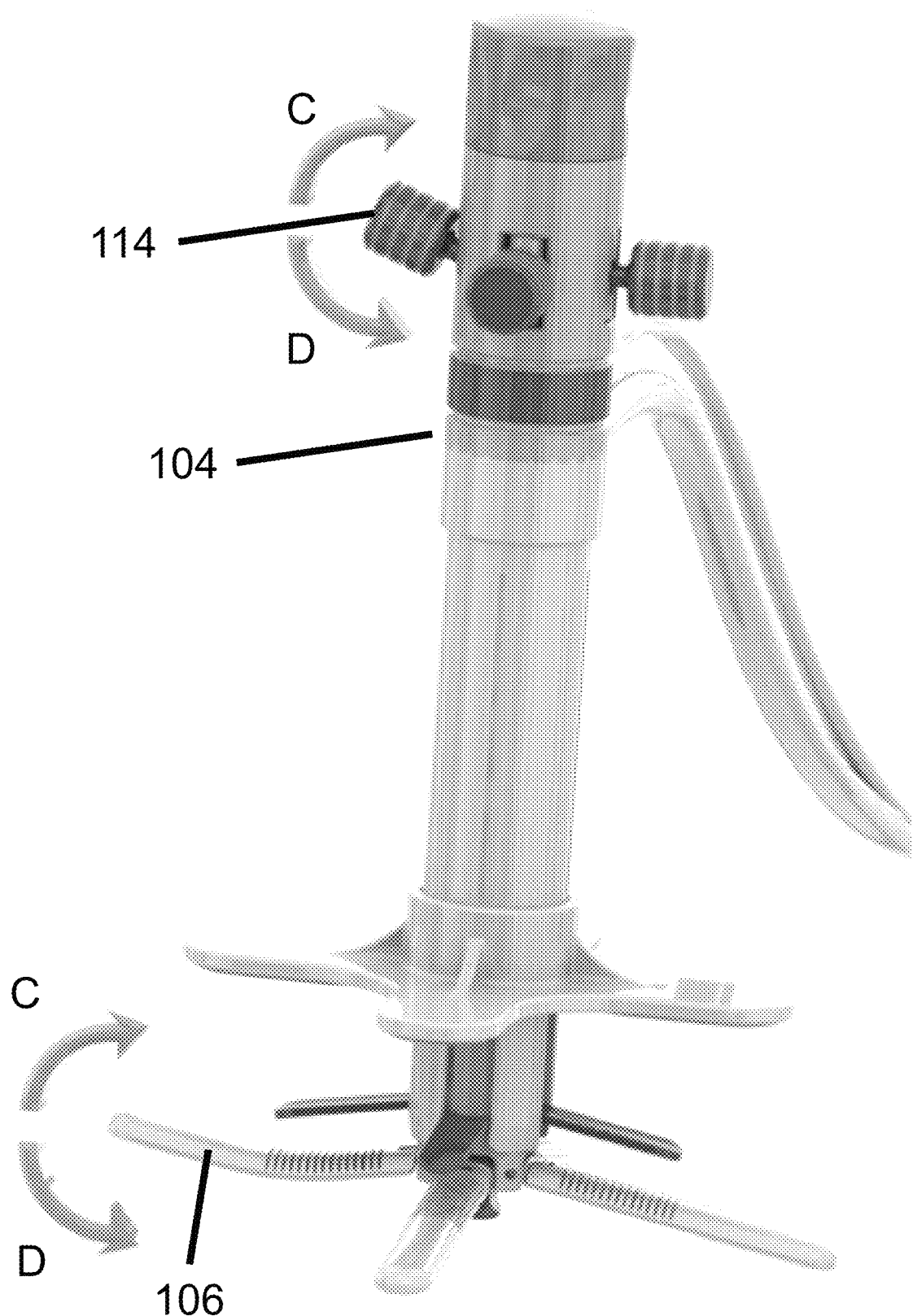
FIG. 7A illustrates the use of joystick controls on the endoscope to individually adjust a pitch of each of the extendible arms along a lateral axis of each individual extendible arm, according to one embodiment of the invention.
Figure 7B:
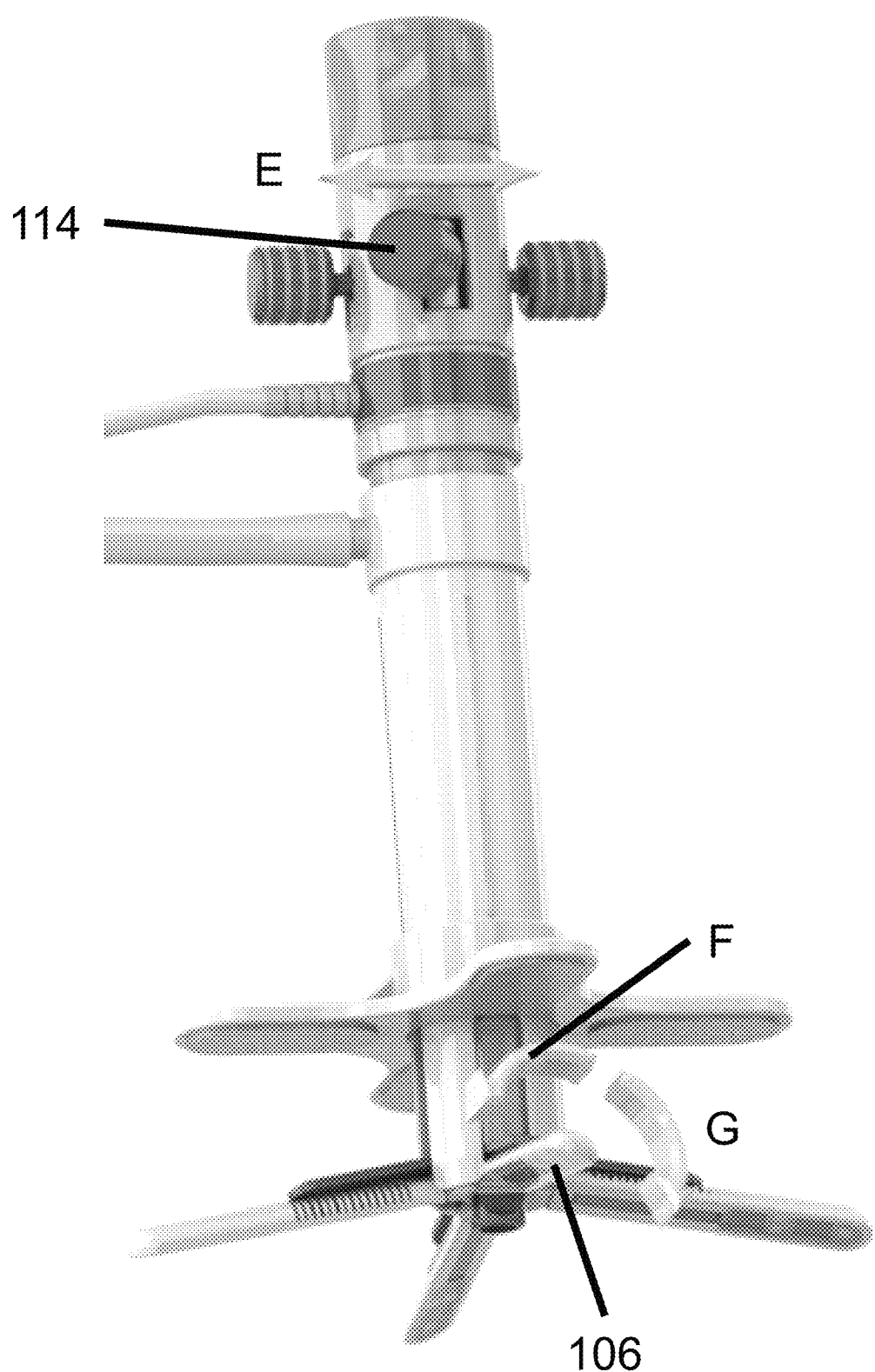
FIG. 7B illustrates the use of the joystick controls on the endoscope to individually adjust a roll of each of the extendible arms along a longitudinal axis of each individual extendible arm, according to one embodiment of the invention.

Additional control of the pitch and roll of the multifunctional arms may be provided as well in order to aid a medical professional in viewing an interior of the abdominal cavity from any angle, as illustrated in FIGS. 7A-7B. In one embodiment, a plurality of joystick controls 114 may be provided on the outer surface of the camera platform 104, each of which can be actuated in directional or rotational movement to correspondingly actuate one or more of the multifunctional arms 106 in a similar directional or rotational movement. As illustrated in FIG. 7A, a vertical directional movement of the joystick 114 along the lines of arrows C and D changes a pitch of the extendible arm 106 relative to its lateral axis. Similarly, as shown in FIG. 7B, a horizontal directional movement of the joystick 114 along the lines of arrow E will create a roll adjustment of the multifunctional arm 106 along its longitudinal axis in order to roll the multifunctional arm 106 from side-to-side along the lines of arrows F and G.

Figure 8A:
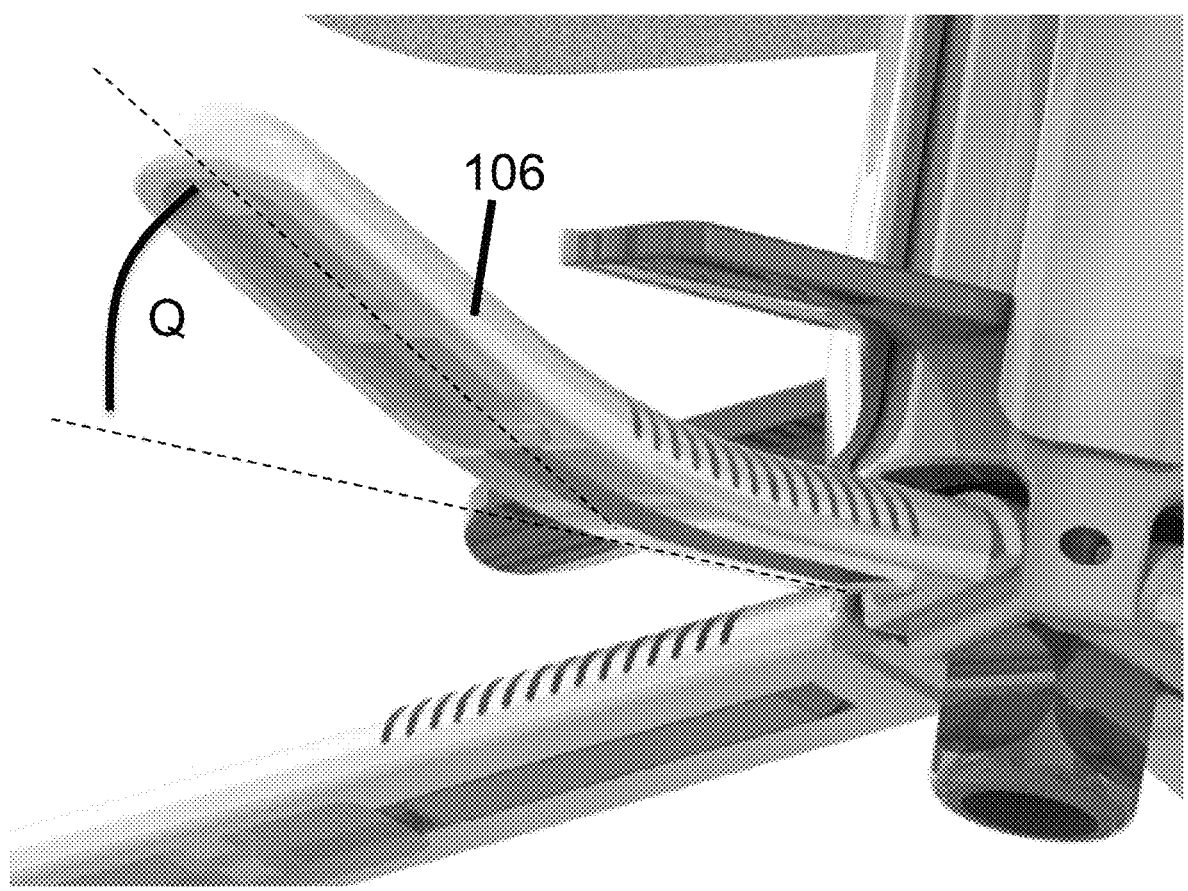
FIG. 8A illustrates a close-up perspective view of the pitch movement of one of the extendible arms along the lateral axis of the extendible arm, according to one embodiment of the invention.
Figure 8B:
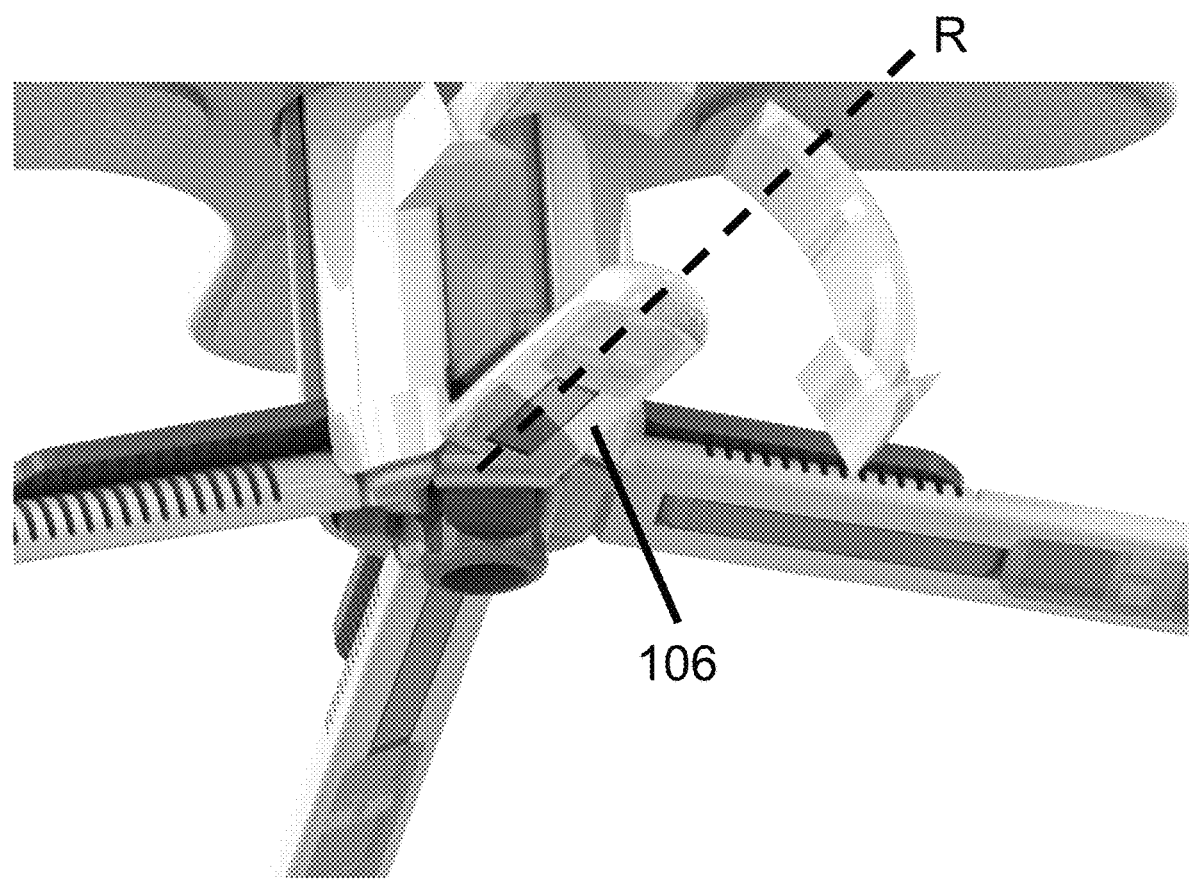
FIG. 8B illustrates a close-up perspective view of the roll movement of one of the extendible arms along the longitudinal axis of the extendible arm, according to one embodiment of the invention.

FIG. 8A illustrates a close-up perspective view of the pitch movement of the multifunctional arm 106 along its lateral axis, as illustrated by the measurement of angle Q. FIG. 8B illustrates a close-up perspective view of the roll movement of the multifunctional arms 106 along its longitudinal axis R. As described above, in one embodiment each arm 106 can be individually controlled with an individual joystick 114 to provide a customized view depending on the circumstances required for an endoscopic procedure. However, it may also be advantageous to provide a synchronous mode which synchronizes the movement of two or more of the multifunctional arms 106 to ensure that they provide similar movement and allow for the creation of stereoscopic or other coordinated images.

Figure 9:
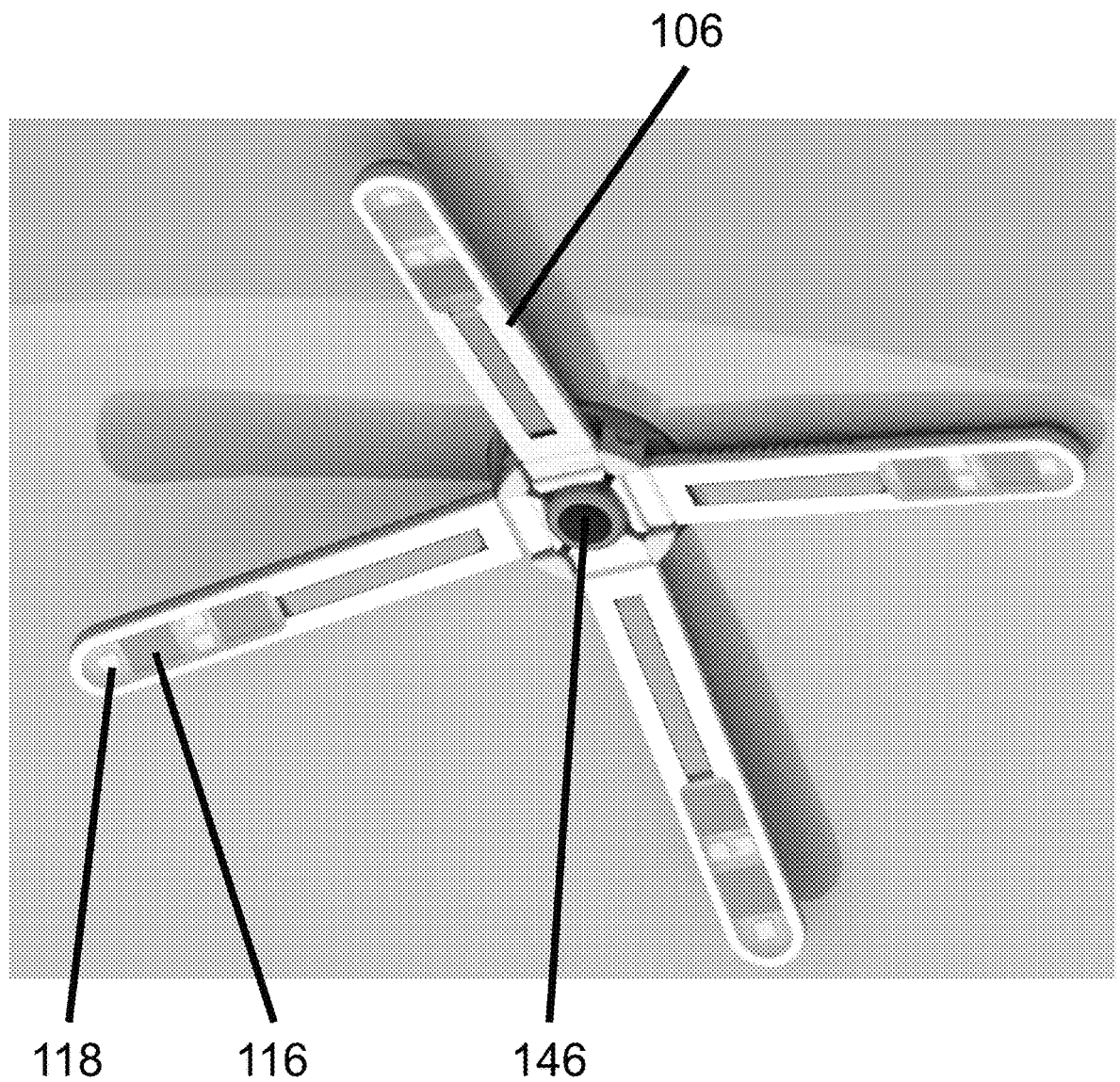
FIG. 9 illustrates a fully-deployed endoscope within a body cavity, according to one embodiment of the invention.

FIG. 9 illustrates a bottom-up perspective view of the fully-deployed endoscope within the body cavity, illustrating the position of the multifunctional arms 106 with respect to one another, as well as the alternative pitches of each arm 106. The cameras 116 and lighting elements 118 are also clearly visible from this view. It should also be noted that the camera platform 104 still provides an opening 146 for passage of an endoscopic tool.

Figure 10:
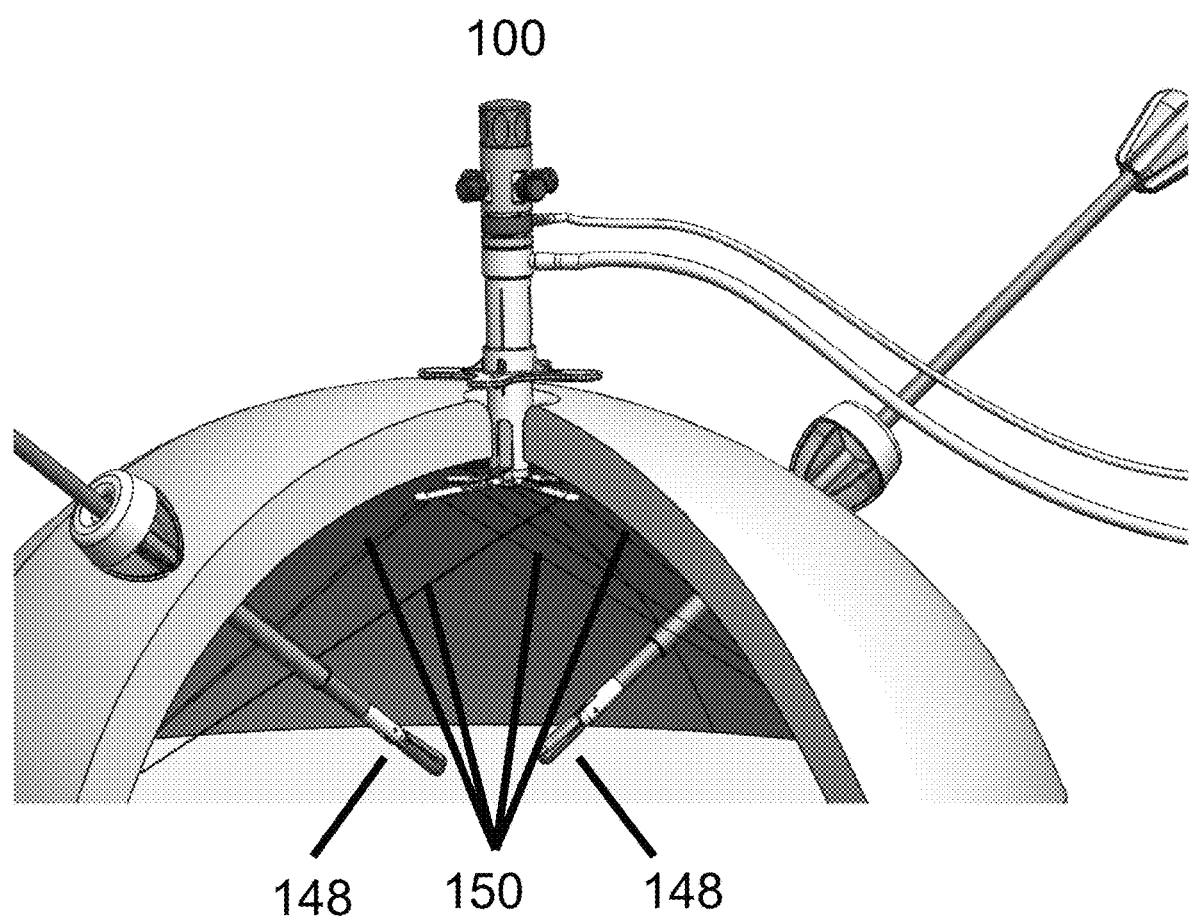
FIG. 10 is a cut-away illustration of a body cavity during an endoscopic procedure, illustrating the endoscope in the fully-deployed configuration within a body cavity, and further illustrating a wide-angle visualization that is provided by the deployment of multiple cameras, lights and sensors capturing images from multiple individually adjustable angles of the extendible arms, according to one embodiment of the invention.

FIG. 10 illustrates a cut-away of the body cavity during an endoscopic procedure, along with the fully-deployed endoscope 100 and adjacent endoscopic tools 148 for performing the procedure. FIG. 10 also illustrates the viewing lines 150 of the imaging devices on the multifunctional arms 106 and the corresponding wide angle view of the abdominal cavity that is provided.

Endoscopic Tool with Integrated Image Capture Device

Figure 11A:
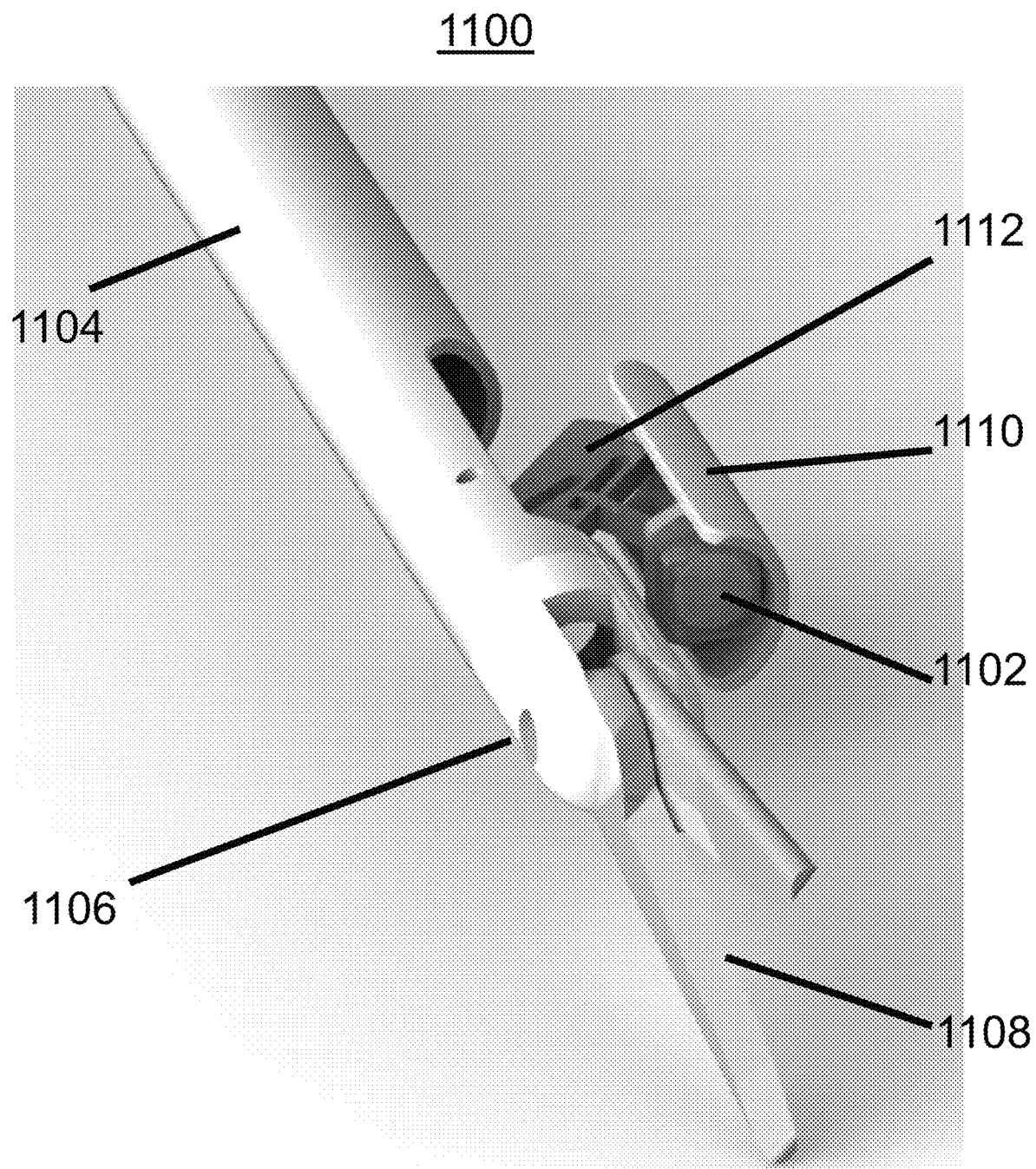
FIG. 11A illustrates an upper perspective view of an endoscopic tool with an integrated camera deployable from a side position of the tool arm, according to one embodiment of the invention.

FIG. 11A illustrates one embodiment of an endoscopic tool 1100 with an image capture device 1102 integrated into a side portion of an arm 1104 of the tool proximate to a distal end 1106 for providing more direct viewing of an area in which a tool 1108 is needed. In this embodiment, the tool 1108 is a pair of scissors disposed at the distal end 1106 of the endoscopic tool 1100, and includes the camera 1102 integrated into the arm 1104 of the tool via an extendible and retractable camera housing 1110 that allows for the camera to be extended both laterally away from the arm 1104 and longitudinally forward in the direction of the tool 1108 to provide for direct viewing of the area around the tool 1108 and the activity of the tool 1108.

The movement of the camera housing 1110 may be accomplished by a hinge mechanism 1112 anchored within the tool arm 1104 which allows the camera housing to pivot out and forward, with the camera 1102 being positioned at the front end of the camera housing 1110. Although the hinge 1112 may be designed to dispose the camera 1102 at an angle parallel to the longitudinal axis of the tool arm 1104, in one embodiment the hinge 1112 provides for further extension of a rear portion of the camera housing 1110 in order to angle the camera 1102 inward and more directly at the tool 1108. In one embodiment, the actuation of the hinge 1112 also acts to activate the electronics for the camera 1102, including any lighting mechanisms that may also be disposed on the tool.

Figure 11B:
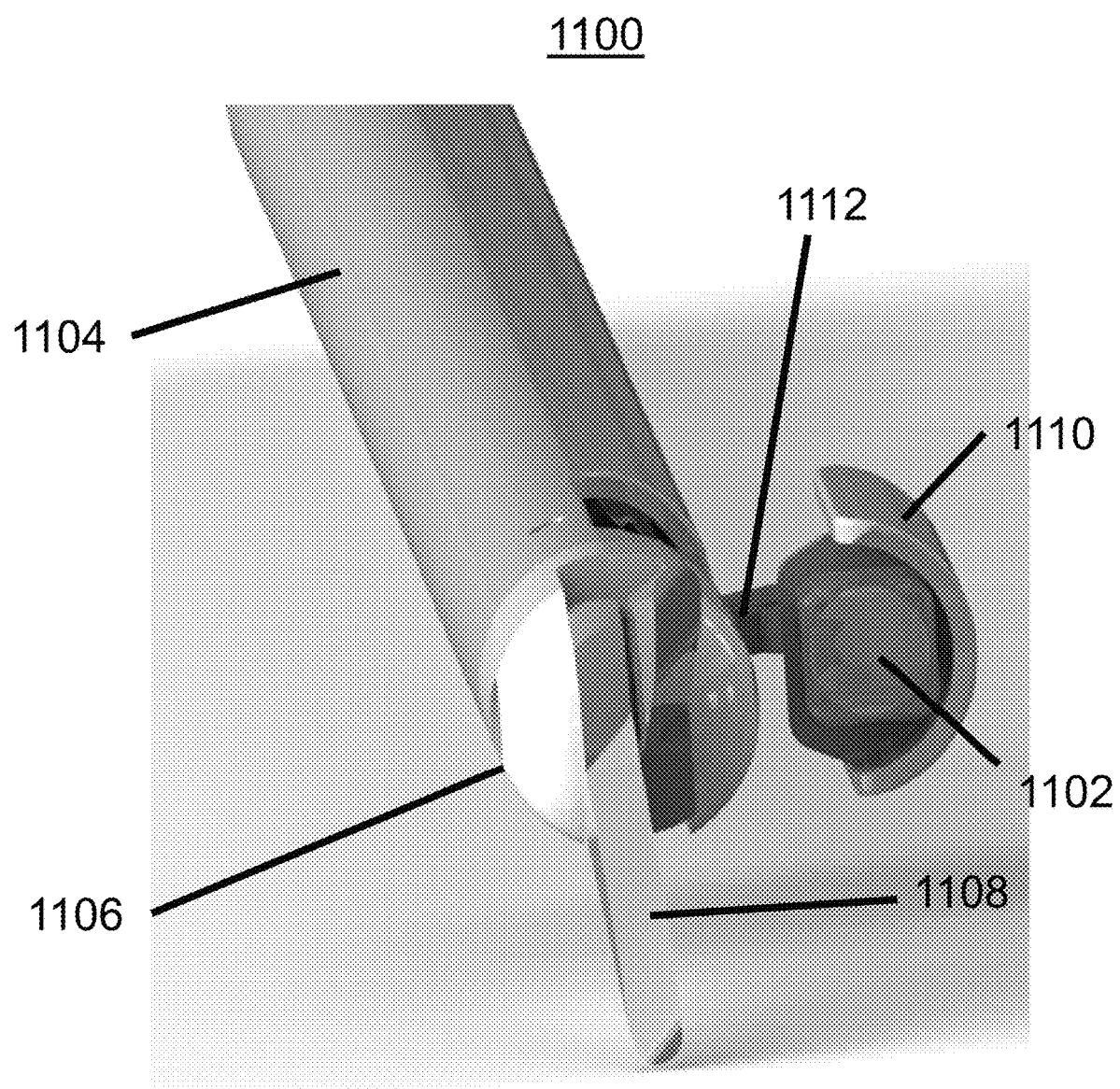
FIG. 11B illustrates a front perspective view of the endoscopic tool and integrated camera, according to one embodiment of the invention.
Figure 11C:
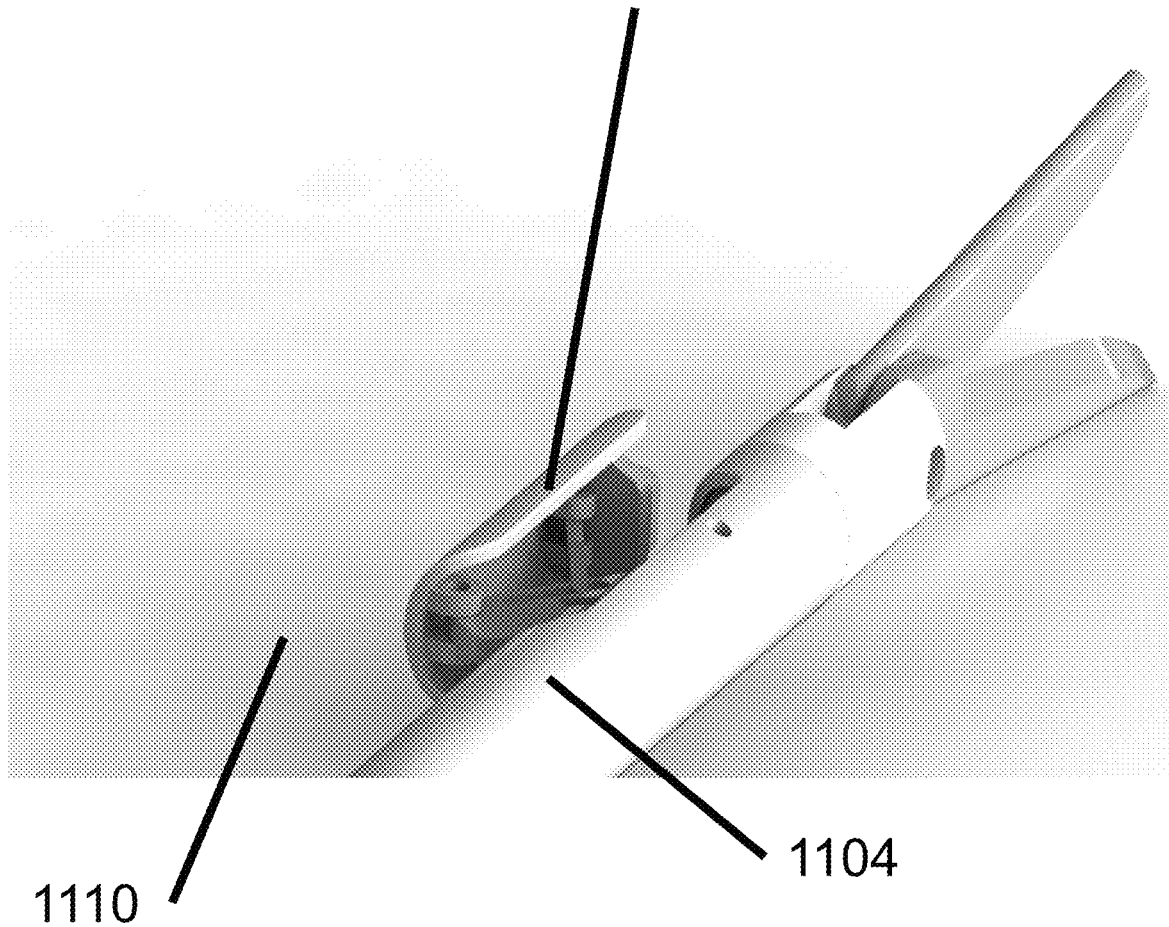
FIG. 11C illustrates a rear perspective view of the endoscopic tool and integrated camera, according to one embodiment of the invention.

FIG. 11B illustrates a front perspective view of the endoscopic tool 1100 to further illustrate the position of the camera 1102 in an extended configuration where the hinge 1112 is fully extended from the arm 1104 to provide a broad view of the distal end 1106 of the tool and activity of the scissors 1108. FIG. 11C illustrates a rear perspective view of the endoscopic tool 1100 illustrating the position of the camera housing 1110 in a partially extended configuration where the camera housing 1110 is only partially extended from the tool arm 1104.

Figure 12A:
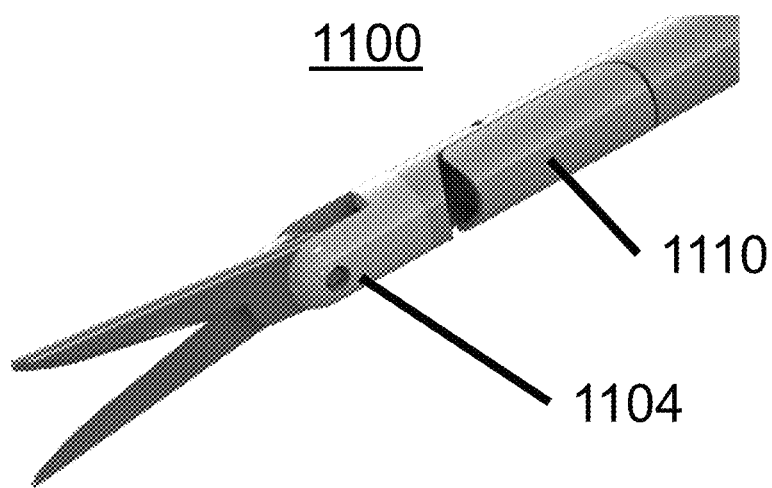
FIG. 12A illustrates the endoscopic tool with the integrated camera in a closed or non-deployed configuration embedded and enclosed within the tool arm, according to one embodiment of the invention.
Figure 12B:
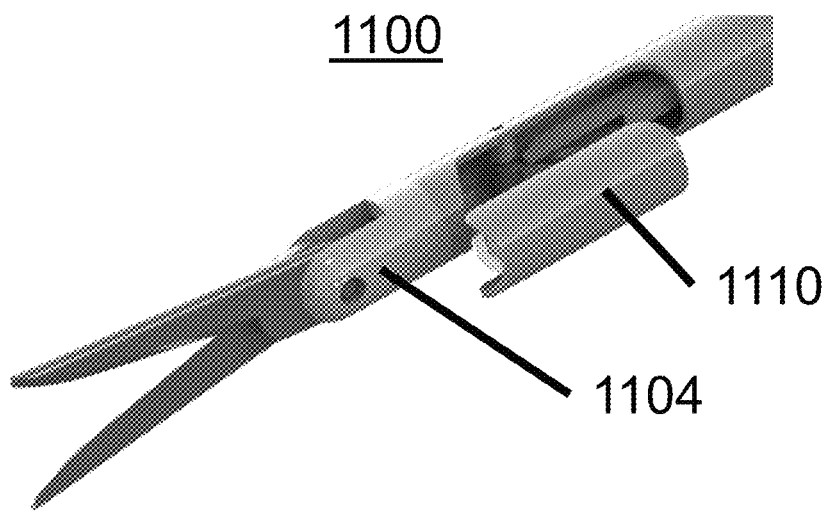
FIG. 12B illustrates a partially-deployed configuration of the integrated camera on the endoscopic tool, according to one embodiment of the invention.
Figure 12C:
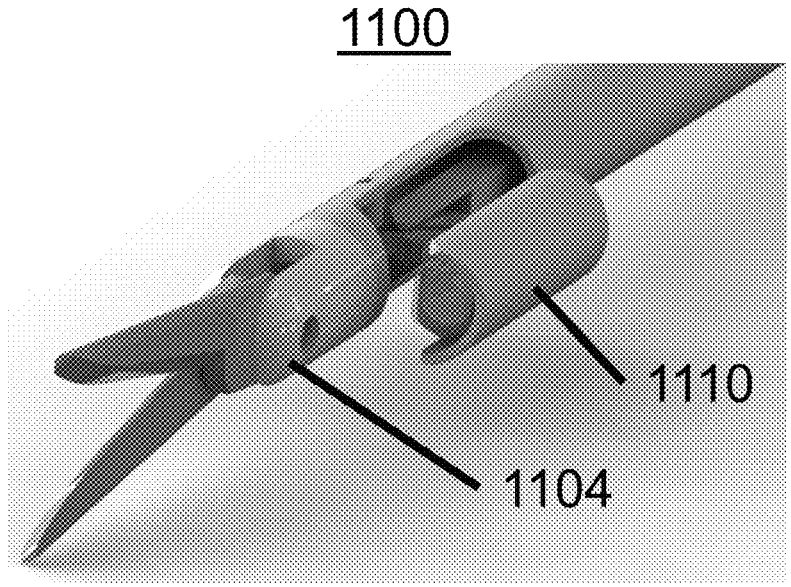
FIG. 12C illustrates a fully-deployed configuration of the integrated camera on the endoscopic tool, according to one embodiment of the invention.

FIGS. 12A-12C illustrate a process of extending the camera 1102 to various distances from the tool arm 1104 in order to provide differing angles of view. FIG. 12A illustrates a closed configuration of the endoscopic tool 1100 where the camera is fully contained within the tool arm 1104, which is advantageous when inserting the endoscopic tool 1100 into an opening in the body cavity. In the closed configuration, the camera housing 1110 is flush against the tool arm 1104. FIG. 12B illustrates the camera housing 1110 in a partially-extended configuration where it has been partially extended away from the tool arm 1104, while FIG. 12C illustrates the camera housing 1110 in the fully-extended configuration at a maximum distance from the tool arm 1104.

Figure 13:
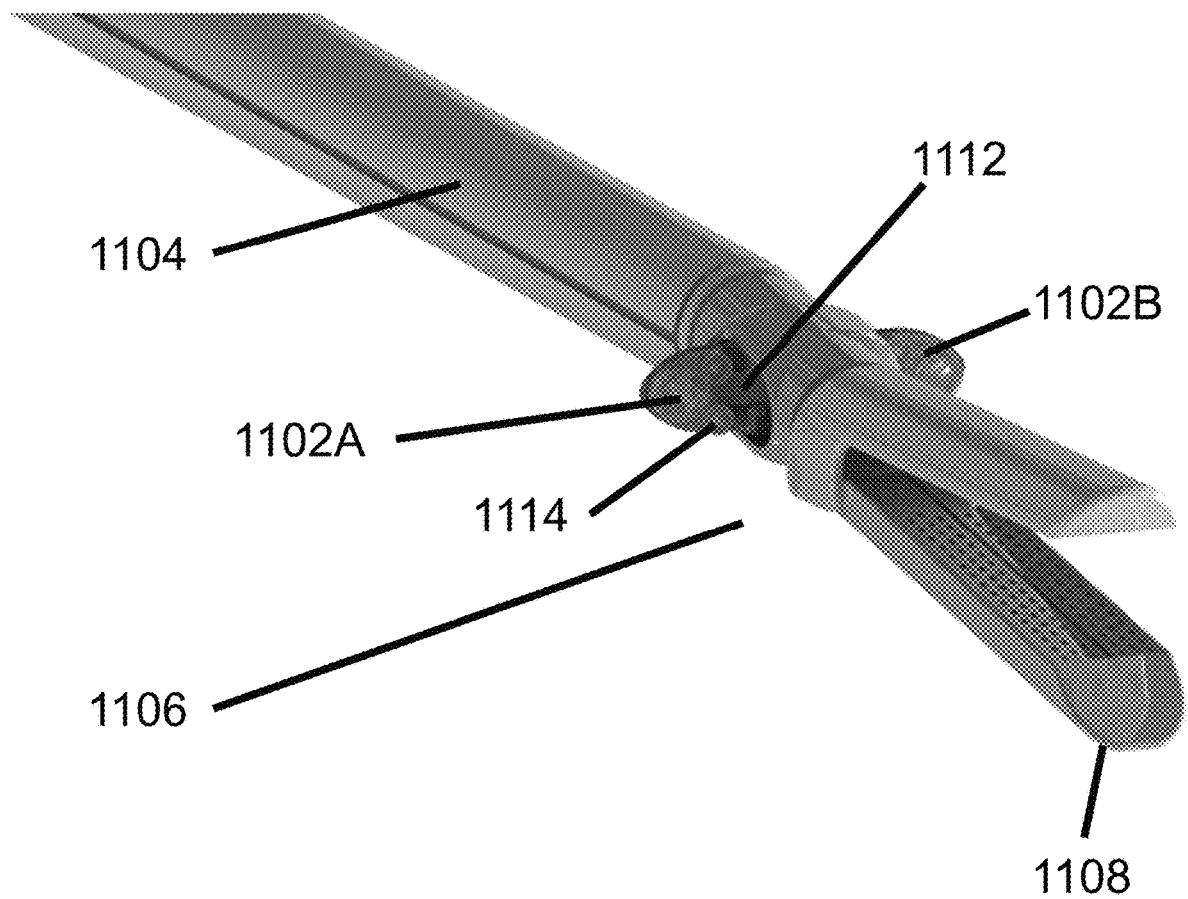
FIG. 13 illustrates an alternative embodiment of the endoscopic tool with dual side-mounted deployable cameras and lights for capturing three-dimensional images, according to one embodiment of the invention.

FIG. 13 illustrates an alternate embodiment of the endoscopic tool 1100, where a plurality of cameras 1102A and 1102B are mounted on opposing sides of the tool arm 1104 at the distal portion 1106, such that they can capture images to produce a three-dimensional image of the activity area around the tool 1108. The hinge mechanism 1112 in this embodiment may be configured differently than above to simply allow for the camera to extend into a fixed angular position approximately perpendicular to the longitudinal axis of the tool arm 1104. Lighting elements 1114 are additionally disposed adjacent to the camera 1102. This embodiment provides an additional useful visualization of a working area of a tool 1108 (in this case, graspers) which may be performing critical tasks during a minimally invasive procedure.

Figure 14A:
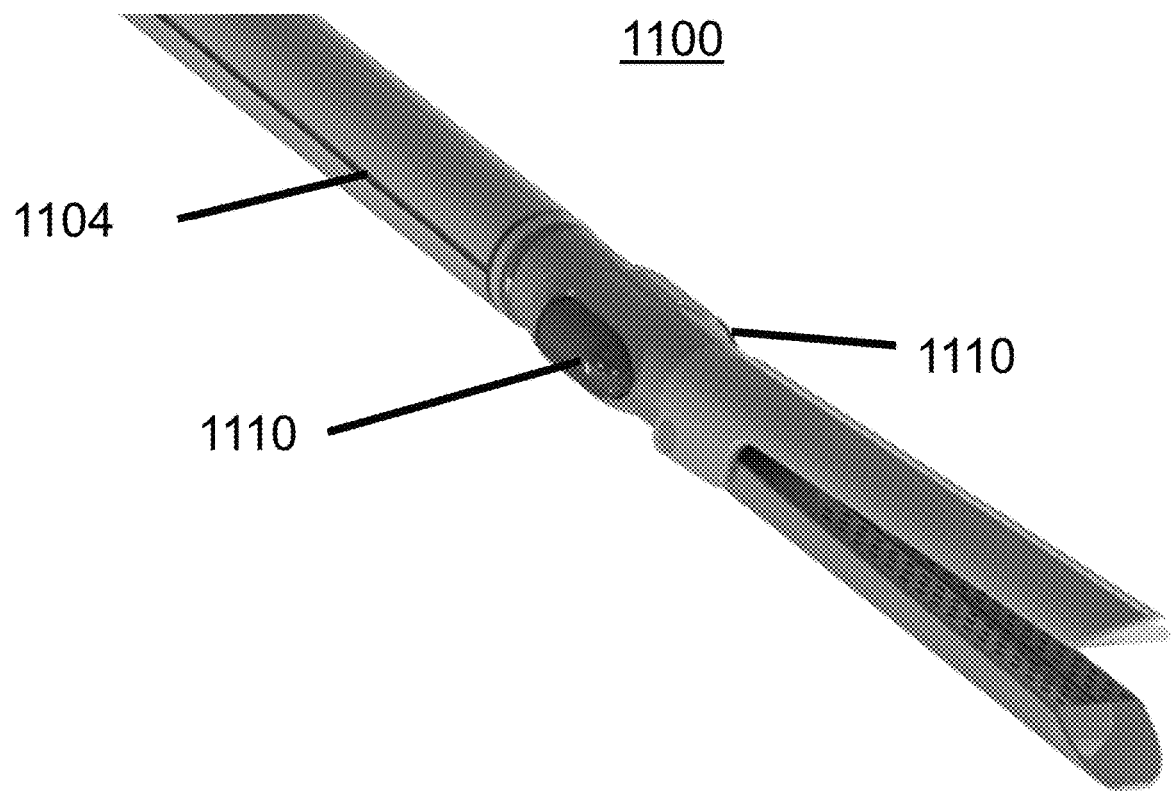
FIG. 14A illustrates a non-deployed configuration of the dual side-mounted cameras on the endoscopic tool, according to one embodiment of the invention.
Figure 14B:
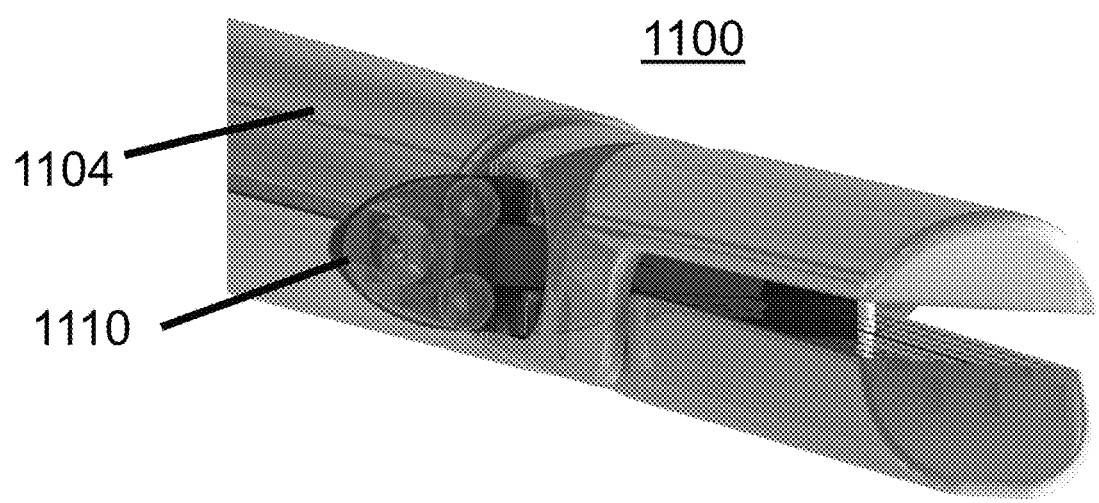
FIG. 14B is a close-up front perspective view illustration of the endoscopic tool with dual side-mounted cameras in a deployed configuration, according to one embodiment of the invention.

FIG. 14A illustrates a closed configuration of the dual-camera endoscopic tool 1100, where the camera housing 1110 is substantially contained within the tool arm 1104 in order to more easily insert the tool 1100 into the body cavity through the central opening. FIG. 14B is a close-up perspective view illustration of the tool 1100 in an open configuration where the camera housing 1110 has fully extended.

System for Capturing Endoscopic Images

Figure 15:
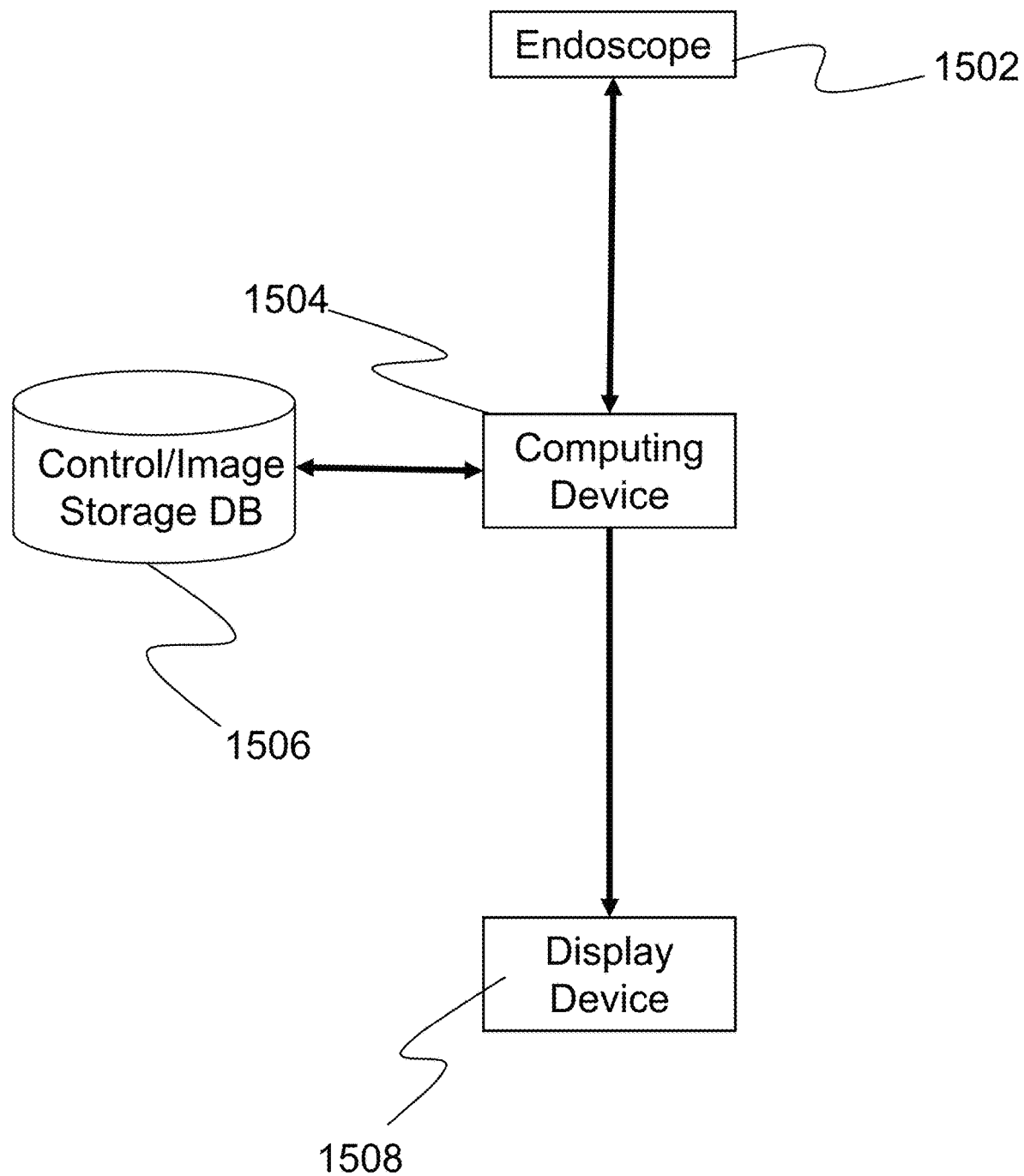
FIG. 15 illustrates a system for capturing images from an endoscope as described herein and transmitting the images to an image processing device for real-time processing and displaying of a three-dimensional image, according to one embodiment of the invention.

In one embodiment, as illustrated in FIG. 15, the endoscope 1502 is able to capture one or more images and other data from the extendible arms and wirelessly transmit the data to a computing device 1504. The computing device may also be configured to wirelessly control the endoscope in order to adjust various angles, extensions and other aspects of the multifunctional arms—individually or jointly—using software to more easily and accurately adjust the optics, angles and other aspects of the endoscope. Control of the lighting, angles and extension of the arms—as well as any integrated tools or other sensors—may be integrated into the computing device. Control protocols and other data may be stored in a connected database 1506.

The computing device may also be responsible for generating a combined image—such as a composite image of the multiple views or a three-dimensional image from one or more of the images captured by the extendible arms and displaying the image on a display device 1508 to a medical professional controlling the endoscope. The display device may be a monitor, television, computer display or a virtual reality headset, which may be connected with the computing device in a wired or wireless configuration. The images may be processed and displayed in real time to provide the medical professional with an improved image of an area of interest. In one embodiment, more than two images may be integrated into a wide-angle view of the abdominal cavity in either two or three dimensions by stitching together the multiple images captured from each image capture device on each extendible arm.

Figure 16:
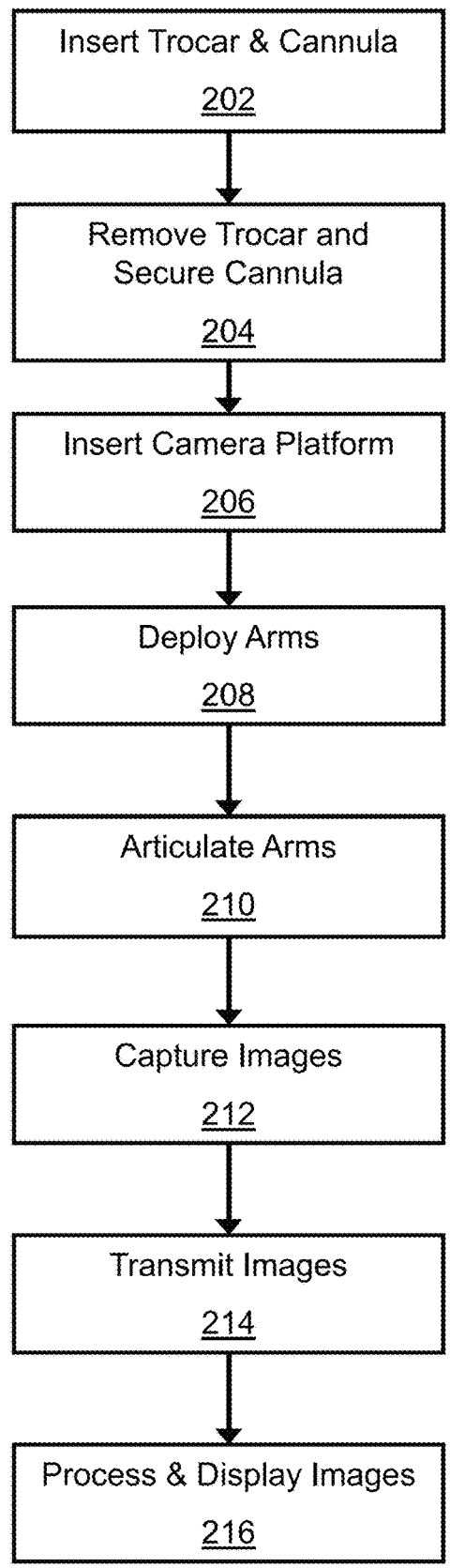
FIG. 16 is a flow diagram illustrating an example process for inserting, deploying, adjusting and capturing images using the endoscope as described herein, according to an embodiment of the invention.
Figure 17:
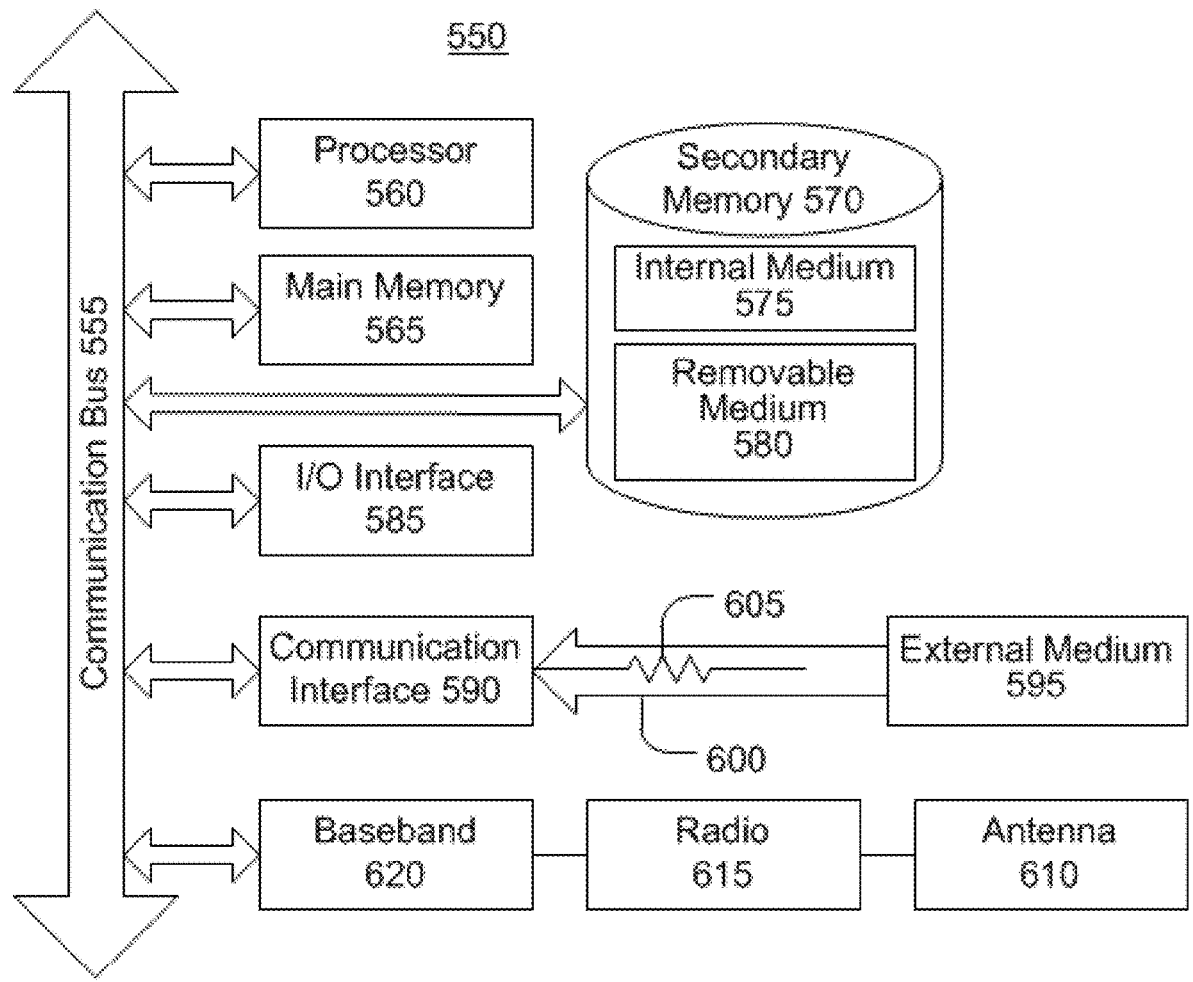
FIG. 17 is a block diagram illustrating an example wired or wireless processor-enabled device that may be used in connection with the various embodiments described herein.

FIG. 16 illustrates on embodiment of a method of implementing the endoscope described above, wherein, in step 202, the cannula and trocar are inserted into the body cavity to form an opening. In step 204, the trocar is removed and the cannula is secured to the body cavity by the support arms and stabilization plate, as described above. In step 206, the camera platform is inserted through the opening in the cannula and into the body cavity, after which, in step 208, the multifunctional arms are deployed. In step 210, the arms are articulated in one or more ways through extension or movement along the longitudinal or lateral axes (roll and pitch) to obtain a desired viewpoint of each arm. In step 212, images are captured by the cameras embedded within each arm and then transmitted in step 214 to a remote computing device, where they can then be processed and displayed to a user in real time in step 216.

Computer-Enabled Embodiment

FIG. 18 is a block diagram illustrating an example wired or wireless system 550 that may be used in connection with various embodiments described herein. For example, the system 550 may be used as or in conjunction with an endoscope, endoscopic tool and computing device as previously described with respect to FIGS. 1-17. The system 550 can be a conventional personal computer, computer server, personal digital assistant, smart phone, tablet computer, or any other processor enabled device that is capable of wired or wireless data communication. Other computer systems and/or architectures may be also used, as will be clear to those skilled in the art.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

System 550 preferably includes a main memory 565 and may also include a secondary memory 570. The main memory 565 provides storage of instructions and data for programs executing on the processor 560. The main memory 565 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 570 may optionally include an internal memory 575 and/or a removable medium 580, for example a floppy disk drive, a magnetic tape drive, a compact disc ("CD") drive, a digital versatile disc ("DVD") drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 570. Examples of external storage medium 595 may include an external hard disk drive or an external optical drive, or and external magneto-optical drive.

Other examples of secondary memory 570 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage media 580 and communication interface 590, which allow software and data to be transferred from an external medium 595 to the system 550.

System 550 may also include an input/output ("I/O") interface 585. The I/O interface 585 facilitates input from and output to external devices. For example, the I/O interface 585 may receive input from a keyboard or mouse and may provide output to a display. The I/O interface 585 is capable of facilitating input from and output to various alternative types of human interface and machine interface devices alike.

System 550 may also include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a modem, a network interface card ("NIC"), a wireless data card, a communications port, a PCMCIA slot and card, an infrared interface, and an IEEE 1394 fire-wire, just to name a few.

Communication interface 590 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

The system 550 also includes optional wireless communication components that facilitate wireless communication over a voice and over a data network. The wireless communication components comprise an antenna system 610, a radio system 615 and a baseband system 620. In the system 550, radio frequency ("RF") signals are transmitted and received over the air by the antenna system 610 under the management of the radio system 615.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit ("IC"). The demodulator and modulator can also be separate components. In the incoming path, the demodulator strips away the RF carrier signal leaving a baseband receive audio signal, which is sent from the radio system 615 to the baseband system 620.

If the received signal contains audio information, then baseband system 620 decodes the signal and converts it to an analog signal. Then the signal is amplified and sent to a speaker. The baseband system 620 also receives analog audio signals from a microphone. These analog audio signals are converted to digital signals and encoded by the baseband system 620. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 610 where the signal is switched to the antenna port for transmission.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 may include various software modules (not shown) that are executable by processor 560.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general-purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. An endoscope with a multifunctional extending arm comprising:
    a central shaft with a distal end and a proximal end, wherein the distal end is configured to be inserted through a cannula and into a body cavity;
    a plurality of multi-functional arms positioned at the distal end of the central shaft, wherein the multi-functional arms are configured to deploy outward from a longitudinal axis of the central shaft;
    wherein a pitch of a distal end of each of the multi-functional arms is controlled by the endoscope such that the distal ends of the multifunctional arms rotate about respective lateral axes of each of the multi-functional arms relative to the central shaft; and
    wherein a roll of each of the multi-functional arms is controlled by the endoscope such that each of the multifunctional arms rotate about their respective longitudinal axes relative to the central shaft through actuation of a rotatable dial at the proximal end of the central shaft.

2. The endoscope of claim 1, wherein a length of each of the multi-functional arms may be extended away from the central shaft along the longitudinal axis of each multifunctional arm.

3. The endoscope of claim 2, wherein the pitch, roll or extension of one of the multi-functional arms may be independently adjusted with respect to each other multi-functional arm.

4. The endoscope of claim 3, wherein the pitch and roll of each of the multi-functional arms is controlled by a joystick disposed on the proximal end of the central shaft.

5. The endoscope of claim 4, wherein the extension of the length of the multi-functional arms along the longitudinal axis of each multifunctional arm is controlled by the rotatable dial.

6. The endoscope of claim 1, wherein at least one of the multi-functional arms deploys outward from its longitudinal axis in an opposing direction from at least one other opposing extendible arm.

7. The endoscope of claim 1, further comprising a cannula disposed around the endoscope and passing through a body cavity wall, the cannula comprising:
    a stabilization plate positioned around a circumference of the cannula and configured to be disposed against an exterior surface of the body cavity wall; and
    a plurality of deployable support tabs extending from a distal surface of the cannula and configured to be disposed against an interior surface of the body cavity wall;
    wherein the stabilization plate is in mechanical communication with the plurality of support tabs such that movement of the stabilization plate along a longitudinal axis of the cannula results in deployment or retraction of the support tabs.

* * * * *